US 6,551,266 B1

(12) United States Patent
Davis, Jr.

(10) Patent No.: US 6,551,266 B1
(45) Date of Patent: Apr. 22, 2003

(54) RHEOLOGICAL TREATMENT METHODS AND RELATED APHERESIS SYSTEMS

(75) Inventor: Richard C. Davis, Jr., Tampa, FL (US)

(73) Assignee: Occulogix Corporation, Clearwater, FL (US)

( * ) Notice: Subject to any disclaimer, the term of this patent is extended or adjusted under 35 U.S.C. 154(b) by 0 days.

(21) Appl. No.: 09/472,903

(22) Filed: Dec. 28, 1999

Related U.S. Application Data

(60) Provisional application No. 60/158,049, filed on Oct. 7, 1999, and provisional application No. 60/114,144, filed on Dec. 29, 1998.

(51) Int. Cl.⁷ .............................................. A61M 37/00
(52) U.S. Cl. ..................... 604/6.09; 604/4.01; 604/6.01
(58) Field of Search ............................. 604/4.01, 5.01, 604/6.04, 6.09, 6.01, 48; 422/44, 45; 210/650

(56) References Cited

U.S. PATENT DOCUMENTS

| | | | | |
|---|---|---|---|---|
| 4,350,156 A | | 9/1982 | Malchesky et al. ......... 128/214 |
| 4,397,747 A | * | 8/1983 | Ikeda ........................ 210/641 |
| 4,402,940 A | | 9/1983 | Nose et al. ................ 424/101 |
| 4,619,639 A | | 10/1986 | Nose et al. .................... 604/8 |
| 4,648,974 A | | 3/1987 | Rosskopf et al. ........... 210/651 |
| 4,708,713 A | | 11/1987 | Lentz ............................ 604/5 |
| 5,276,611 A | | 1/1994 | Ghiraldi ................ 364/413.03 |
| 5,286,449 A | | 2/1994 | Kuroda et al. ............... 422/48 |
| 5,536,412 A | | 7/1996 | Ash ........................... 210/645 |
| 5,606,976 A | | 3/1997 | Marshall et al. ........... 128/671 |
| 5,720,921 A | | 2/1998 | Meserol ....................... 422/44 |
| 5,722,418 A | | 3/1998 | Bro ............................ 128/732 |
| 5,733,254 A | | 3/1998 | Jones et al. .................... 604/4 |
| 5,734,837 A | | 3/1998 | Flores et al. ............... 395/207 |
| 5,781,442 A | | 7/1998 | Engleson et al. ...... 364/478.02 |
| 5,782,792 A | | 7/1998 | Jones et al. .................... 604/5 |
| 5,922,278 A | * | 7/1999 | Chapman et al. ............. 422/22 |
| 6,245,038 B1 | | 6/2001 | Borberg et al. ........... 604/5.01 |

FOREIGN PATENT DOCUMENTS

| | | | |
|---|---|---|---|
| EP | 0041350 | 12/1981 | ............ A61M/1/03 |
| EP | 0120445 | 10/1984 | ............ A61M/1/03 |
| WO | WO 90/14850 | 12/1990 | |
| WO | WO 97/49047 | 12/1997 | ........... G06F/17/30 |
| WO | WO 98/02836 | 1/1998 | |

OTHER PUBLICATIONS

Allikmets et al., Mutation of the Stargardt disease gene (ABCR) in age–related macular degeneration, *Science*, (1997) 277:1805–1807.

Berrouschot et al., Extracorpeal membrane differential filtration—a new and safe method to optimize hemorheology in acute ischemic stroke, *Acta Neurol. Scand.* (1998) 97:126–130.

Brunner et al., Clinical efficacy of haemorheological treatment using plasma exchange, selective adsorption and membrane differential filtration in maculopathy, retinal vein occlusion and uveal effusion syndrome, *Transfus. Sci.* (1996) 17:493–498.

(List continued on next page.)

*Primary Examiner*—Manuel Mendez
(74) *Attorney, Agent, or Firm*—Morgan, Lewis & Bockius LLP

(57) ABSTRACT

Therapeutic apheresis treatments and diagnostic monitoring methods are described, specifically relating to the depletion and/or removal of a broad bandwidth of certain rheologically active elements from the blood of a patient followed by return of the blood so treated to the patient, and to methods or procedures of apheresis treatment, especially biophysiologic blood filtering treatments and computer medicated delivery methods configured to provide such apheresis treatments to patients with certain chronic, age-related, degenerative, atherogenic, thrombotic or inflammatory diseases; especially those associated with RAM accumulation-deposition causing disturbances of blood rheology or microcirculatory impairment.

15 Claims, 2 Drawing Sheets

OTHER PUBLICATIONS

Brunner et al., Change in hemorrheological and biochemical parameters following membrane differential filtration, *Int. J. Aritif. Organs* (1995) 18:794–798.

Brunner et al., Erythrocyte apheresis in combination with elimination of fibrinogen and plasma proteins of higher molecular weight in macular disease and in uveal effusion syndrome, *Acta Medica Austriaca* (1991) 18(supp):63–65.

Davis & Klingel, Exploring RheoTherapy's impact on ARMD, Optometry Today, http://www.optometrytoday.com/ces/rheotherapy/lesson.html (posted Oct. 7, 1998).

Euler et al., Plasma exchange in systemic lupus erythematosus, *Transfus. Sci.* (1996) 17:245–265.

Friedman et al., A hemodynamic model for the pathogenesis of age–related mascular degeneration, *Am. J. Ophthalmol.* (1997) 124:677–682.

Grunwald et al., Effect of panretinal photocoagulation on retinal blood flow in proliferative diabetic retinopathy, *Ophthalmology* (1986) 93:590–595.

Harada et al., Therapeutic apheresis for renal diseases, *Ther. Apher.* (1998) 2:193–198.

Inhoffen & Nüβgens, Rheological studies on patients with posterior subretinal neovascularization and exudative age–related macular degeneration, *Graefes Arch. Clin. Exp. Ophthalmol.* (1990) 228:316–320.

Lentz, The role of therapeutic apheresis in the treatment of cancer: a review, *Ther. Apher.* (1999) 3:40–49.

Matsuda et al., An effective LDL removal filter for the treatment of hyperlipidemia, *Artif. Organs* (1995) 19:129–134.

Russo et al., Haemorheological changes in mixed cryoglobulinaemia during apheresis treatment, *Transfus. Sci.* (1996) 17:499–503.

Siami et al., Cryofiltration apheresis for treatment of cryoglobulinemia associated with hepatitis C, *ASAIO J.* (1995) 41, M315–M318.

Widder et al., Changes of haemorheological parameters when using plasma exchange, selective adsorption and membrane differential separation, *Transfus. Sci.* (1996) 17:505–510.

Widder et al., Changes of visual acuity in patients with age related macular degeneration (AMD) after elimination of high molecular weight proteins and lipids, *Investigative Ophthalmology & Visual Science* (1997) 38:460–B371.

* cited by examiner

RHEOLOGICAL TREATMENT METHODS AND RELATED APHERESIS SYSTEMS

RELATED CASES

This application is based on U.S. Provisional Application Ser. No. 60/114,144, filed Dec. 29, 1998 and U.S. Provisional Application Ser. No. 60/158,049, filed Oct. 7, 1999, these applications being hereby incorporated by reference in their entirety.

FIELD OF THE INVENTION

The invention relates generally to the treatment of various disorders caused by or associated with relatively elevated levels of certain high molecular weight blood plasma components, particularly those rheologically active macromolecules that generally are larger than about 500,000 Daltons (500 kDa) in weight or greater than about 200 Å in diameter. Elevated levels of such plasma constituents are found in chronic, age-related, degenerative, and/or inflammatory diseases associated with the accumulation of and/or deposition of biological substances that result in or are associated with disturbances of blood rheology, extra-cellular matrix composition, and intrinsic endothelial cell function. The invention relates specifically to Rheopheresis® blood filtration treatments, and associated membrane differential filtration devices, methods, treatment apparatus and systems for such diseases, and more particularly to the treatment of atherosclerotic and/or thrombotic diseases such as coronary, renal, peripheral and cerebrovascular diseases as well as perfusion deficit diseases such as Age-related Macular Degeneration (AMD), Diabetes, Rheumatoid Arthritis and Alzheimer's Disease. Such methods include but are not limited to VasoTherapy™ and AngioTherapy™ using the RheoFilter AR 3000 and RheoFilter AR 4000 hollow fiber membranes respectively. Thus, for the purposes of this application, as will be evident from the context, the term "rheopheresis" applies broadly to each of methods and filters collectively, although they include different products, are directed toward different disease manifestations and are studied, labeled, tested, approved, utilized and reimbursed differently.

BACKGROUND OF THE INVENTION

Circulating blood components that are suspended in or dissolved in the plasma can be loosely classified into (1) small (low molecular weight compounds), (2) medium or "middle molecules" and (3) large (high molecular weight compounds). The relationship between the size and weight of these compounds is determined by: (1) their density, which is directly related to the three-dimensional conformational structure (protein folding) of the isoform expressed and (2) their biologically active form (monomer vs. multimer). Small plasma compounds are typically less than 75 Å in their shortest axis diameter and have low molecular weights generally less than about 120,000 Daltons (120 kDa). Middle molecules occupy the range roughly from about 75 Å to 150 Å in their shortest axis diameter, weighing 120 kDa to 500 kDa. Large plasma components are those typically larger than about 150 Å in their shortest axis diameter weighing generally greater than 500 kDa.

Typical low molecular weight moieties include substances such as albumin (69 kDa) and certain cytokines such as tumor necrosis factor (TNF- alpha) and certain growth factors (VEGF, TGF- beta, etc.). Middle molecules may include the gamma immune globulins (~125 kDa) and similar-sized particles. The high molecular weight group includes the "rheologically active macromolecules" (RAM) compounds such as the alpha-2 macroglobulin tetramer (~900 kDa), lipoproteins A and B, cholesterol isoforms (VLDL, LDL, IDL, etc) and other beta lipoproteins(~850 kDa), fibrinogen, IgM, and many others. Many of these compounds can exist in numerous related isoforms, such as racemers, enantiomers, oxidized and reduced forms, and so on. Frequently, the biologically active state of plasma component particles is conferred in multimeric conformations such as IgA pentamers, TNF- alpha dimers, vitronectin 16-mers and von Willebrand trimers. Often their biological activity will change depending upon the isoform expressed. They are often categorized into groups, classes, families, and superfamilies.

Many high molecular weight RAM compounds are associated with various diseases that may be treated according to the methods of the present invention.

1. Diseases Associated with High Molecular Weight Compounds in the Plasma

Historically, diseases have been classified as being either 'acute' or 'chronic' in nature. Recently it has been determined that many chronic illnesses, especially some age-related, degenerative, and inflammatory diseases, result from pathologies involving either: (1) a slowly progressive, chronic, time-dependent accumulation of biological moieties into tissues comprised, in some cases, of metabolic debris, or (2) in other cases of the rapid, acute, up-regulated overproduction of these same substances where they can exhibit acute phase reactant behavior.

Irrespective of their origin, mechanism of formation or temporal generation, in those disease states referenced above, these biological products have a tendency to collect within peri-endothelial, capillary, interstitial, and extracellular matrix tissues. Although they are typically distributed across all three body compartments (intravascular, interstitial and intracellular), depending upon their equilibrium constants and the homeostatic disruption, they will often manifest as increased plasma or serum concentrations within the blood circulation itself. Often, these biological compounds are further modified by acetylation, glycation, oxidative or other processes to form less stable isoforms that condense into complex aggregates (atherosclerotic plaques, drusen, neurofibrillary tangles, lipofuscin, amyloid, etc.). Although these aggregates are comprised primarily of proteinaceous moieties, they also contain lipids, lipoproteins, fatty acids, carbohydrates, metals and other non-protein compounds. Thus, the terms "protein accumulation-deposition diseases" or "dysproteinemias" as has been historically applied to these conditions, is technically a misnomer. Therefore, for the purposes of this application, the term "RAM accumulation-deposition diseases" will be substituted for clarification where appropriate.

Saturated catabolic mechanisms predispose RAM to progressive concentration increases within the blood that primarily and secondarily induce numerous functional disturbances of the endothelium, blood rheology, extra-cellular matrix, microcirculation and/or microperfusion. Elevated serum levels of RAMs have been documented to: (1) cause increases in whole blood and plasma viscosities thus reducing blood flow; (2) promote cell-cell adhesion causing thrombosis, cell clumping and diapedesis; (3) disrupt numerous intrinsic endothelial cell functions, and (4) cause numerous other pathologies which can promote various disturbances in the microcirculation. Such actions are measurable as decreases in capillary perfusion, endothelial cell rupture, atherogenesis, thrombosis, angiogenesis, and other pathological states leading to ultimate end-organ dysfunction or outright failure. Occasionally, primary rheologic pathologies can be so significant that the disturbances can be observed even within the systemic circulation forming procoagulant states and in the extreme - hyperviscosity syndromes, diffuse intravascular coagulation, etc.

Some examples of medical conditions that may be classified as RAM accumulation-deposition diseases are:

Atherosclerotic disease which develops as a result of progressive endothelial cell dysfunction in the presence of progressive deposition of lipid-laden plaques that form preferentially within the intimal walls of coronary, renal, carotid, aortic and certain other arteries throughout the body, often in the presence of hyperlipidemia.

Rheumatoid arthritis which results from the destructive inflammatory reactions occurring in a synovial pannus associated with elevated serum levels of Rheumatoid Factor, various inflammatory proteins, immunologic globulins, integrins, and other compounds, including the chemotactic attraction of activated inflammatory cells, that contribute to the dysfunctional synovial lining of the various joints involved;

Diabetes mellitus which is classically described as an autoimmune disease demonstrating profound pathological effects on the microcirculation and peripheral nervous system, with classically observed disruptions of blood rheology associated with aldose deposition, and other disruptions including: advanced glycation, carbohydrate dysmetabolism, insulin resistance and other pathophysiologic disturbances measured in both the serum and tissues;

Alzheimer's disease which is associated with the formation of "neurofibrillary tangles" or accumulations of complex deposits comprised primarily of Tau proteins and beta-amyloid proteins in specific brain tissues, and is also associated with decreased local blood flow to those same brain tissues;

Age-related macular degeneration ("AMD"), which is often characterized by the deposition of vitronectin, lipofuscin aggregates called drusen and basilar laminar deposits which form within specific retinal tissues (the retinal pigment epithelium/Bruch's Membrane complex) and is associated with a disruption of the choriocapillary microcirculation, as well as observed increases in the serum levels of certain circulating RAMs (cholesterol, fibrinogen, etc.).

Procoagulant State which is often characterized by (relatively increased serum concentrations of certain thrombogenic macromolecules causing) a tendency to relatively more readily activate the coagulation cascade in a patient.

2. Rheolozically Active Macromolecules (RAMs)

RAMs are typically large, high molecular weight biological moieties, comprised primarily of proteins and lipids, and secondarily of fatty acids, carbohydrates and other compounds that are found in the general blood circulation, in the membranes of blood cells, expressed on cell surfaces (especially endothelial cells), deposited in the extra-cellular matrix and within the interior of cells of certain tissues. RAMs are associated with unique pathological roles and physiological effects as described above.

In addition to their unique biochemical roles, RAMs exert numerous secondary and tertiary effects on the blood and blood rheology processes, including acting as buffers, osmotic agents, oncotic agents, signaling molecules, and so on. More specifically, many RAMs exert complex, simultaneous and integrated rheological effects on the blood cells themselves including: (1) red cell aggregation and viscoelasticity; (2) leukocyte adhesion, morphogenesis and diapedesis; and (3) platelet rouleaux formation. These actions are primarily mediated by the regulatory effects of RAM on gene activation and surface receptor expression on these blood cells, and ultimately reflect on both whole blood and plasma viscosities, with primary control over blood flow, shear stress and perfusion within the microcirculation. These effects are transmitted to the macrocirculation via the vasovasorum that nourishes the entire vascular system. Recent research also points to certain RAMs acting as triggers for various gene expressions, and mRNA transcription activity as well, especially in their role in apoptosis (programmed cell death).

Examples of circulating soluble or suspended RAMs commonly measured in the serum of patients are: alpha-2 macroglobulin, fibrinogen, triglycerides, beta-lipoproteins like LDL cholesterols (especially the oxidized forms), fibronectin, vitronectin, IgM, and other immunoglobulins, von Willebrand factor, lipoprotein A, to name just a few. Of course, there are some RAMs less than 500 kDa, however most RAMs are greater than 500 kDa. One object of the present invention is the safe, rapid, efficient and simultaneous depletion of at least two or more of these RAMS from the systemic circulation and by their extraction from the tissues. The close association of these markers and the diseases that they herald and/or play a causative role, allow these moieties to be commonly referred to as "risk factors" or "serological markers" for the development of the diseases with which their serum elevations are correlated (heart disease, stroke, renal failure, blindness, etc., in association with cholesterol, fibrinogen, etc.)

3. Apheresis to Modulate Plasma Levels of RAMs

It is now widely accepted that RAM either directly or indirectly participate in the control of virtually every aspect of vascular cellular metabolic activity. They govern the intricate balance of action and reaction that controls the many complex biochemical reactions necessary to maintain health (homeostasis). The precise homeostatic control mechanisms vary from one endothelial population to another, but generally speaking, most RAM can be classified into having one of two actions, promoters—which activate or "up-regulate" a particular biological action, pathway or process—and inhibitors—which suppress or "downregulate" a particular biological action, pathway or process. Interestingly, depending upon their local concentration levels, many RAM can exhibit both actions—acting like biological switches.

In health, the body responds to the overproduction or under-catabolism of a particular substance by increasing its endogenous production of mediators, which can include a cascade of promoters, inhibitors, or both, as the case may be designed to reduce its concentration back down to normal limits. Conversely, any underproduction or over-catabolism is counteracted with a concomitant release of mediators that likewise can include a cascade of promoters, inhibitors, or both, as the case may be designed to increase its concentration back up to normal limits. Any prolonged disruption of this delicate balance of promoters and inhibitors can lead to a pathologic deterioration of the clinical state into conditions that ultimately manifest themselves as disease. Many diseases manifest themselves as deficiencies of essential macromolecules, RAM accumulation-deposition diseases are easily differentiated by characteristically being associated with excessive concentrations of macromolecules. It is now thought that these imbalances are initially manifested at the molecular level where chemical reactions located in sub-cellular organelles, usually under protein (enzymatic/hormonal) control, determine the ultimate overt clinical status. However, within the bloodstream itself, numerous homeostatic mechanisms have evolved that are regulated not only by the chemical reactions of certain moieties, such as RAMs, but also are directly affected by the absolute plasma concentrations of these components in circulation, such as the rheologic effects. Often, these effects can be greatly accelerated and exaggerated as can be seen in organ failure like the nephrotic syndrome where intravascular plasma losses induce artificially elevated plasma concentrations of RAMs.

A. Plasmapheresis

Increasingly sophisticated apheresis technologies have contributed to advanced methods of providing the two basic forms of apheresis treatment, namely plasmapheresis and cytapheresis. Plasmapheresis involves the extracorporeal manipulation, depletion and/or removal of certain soluble or suspended elements in the plasma portion of the blood, and then returning the blood so treated to the patient to induce a desired clinical effect. Historically, these methods have been primarily concentrated on modulation of immune pathologies. Plasmapheresis is variously performed in vivo using therapeutic plasma exchange (TPE), immunoadsorption (IA), precipitation (HELP), membrane differential filtration (MDF), and other means.

By way of example, one type of plasma filtration column is described in U.S. Pat. No. 4,619,639 (which issued to Asahi Medical Company, Ltd. in 1986).

B. Cytapheresis

Cytapheresis can be distinguished from plasmapheresis in that it involves the extracorporeal manipulation or depletion and/or removal of various circulating or marrow-bound cellular elements in the blood (red cells, white cells, stem cells or platelets) or specific subpopulations of these cells in order to induce a desired clinical effect. Historically, these effects have been primarily concentrated on modulation of hypercellular pathologies like leukemias, myelomas etc. It is variously performed with centrifuge, membrane differential filtration, and other means.

C. Apheresis Equipment

Several new apheresis methods including membrane differential filtration (MDF) systems, utilizing for instance the PlasmaFlo® OP-05(W)L and the RheoFilter® AR2000 blood filters, both manufactured by Asahi Medical Company, Ltd. of Japan, and other such devices, have recently been introduced. These filter combinations have demonstrated the ability to safely and effectively reduce significant concentrations of a broad bandwidth of numerous circulating plasma macromolecules, including; alpha-2 macroglobulin, triglycerides, the cholesterol family of beta-lipoproteins, various immunoglobulins, fibrinogen, advanced glycation modified end products (i.e., AGE-modified lipoproteins), and the like. These MDF apheresis devices employ sophisticated membranes that utilize the presence of porous hollow fibers that sieve out various blood constituents depending upon the pore size in the fiber's sidewall. Accurate control of the average pore size of the fibers within the filters enables one to selectively sieve out only the particular size or weight macromolecules desired above a certain "cut-off" threshold. The RheoFilter AR 2000 for example, has average pore sizes of 250 Å in diameter (about the size of the typical LDL molecule). In theory, depending upon the pore size cut-offs, several filters of differing pore sizes can be placed in series to remove specific components from the blood of virtually any size range.

Other benefits of MDF systems include the application of plasma separation as that performed by the Plasmaflo OP-05 (W)L that operates using low operating trans-membrane pressures such that virtually no hemolysis of the blood occurs during treatment. This represents a significant advance over the centrifuge technologies currently in wide use in the United States and elsewhere. As would be expected, wherever hollow fiber membranes have been introduced, the use of centrifuge systems has been significantly reduced.

4. Various Diseases Treated by Apheresis

A variety of apheresis treatments have been described over the past thirty years for use with patients having acute illnesses. However, patients with chronic, age-related, degenerative, or inflammatory diseases, especially those manifesting disturbances of blood rheology, differ significantly from the historical acutely ill populations that heretofore have obtained plasmapheresis treatment. For example, chronically ill patients are typically significantly older than patients with acute conditions, often have significant co-morbidities (heart disease, etc.), consume numerous medications, and in general are typically less robust (resilient) than the younger acute patient group. Among other things, since many of the chronic, age-related, degenerative, inflammatory diseases are initiated, moderated, or otherwise associated with a disruption of capillary blood flow and/or a dysregulation of microperfusion to a diseased or failing organ and such a condition is typically systemic, other organ systems may be diminished in their intrinsic functional capacities as well. Accordingly, the use of apheresis to treat such chronically ill patients has been relatively limited. One recent exception is hyperlipidemia.

A. Hypercholesterolemia

Several apheresis systems have recently has been introduced for the treatment for patients with clinically evident, refractory, drug resistant, Type II Familial Hypercholesterolemia - a rare chronic, slowly progressive, ultimately fatal illness. (Matsuda et al., (1995) Artificial Organs 19, 129–134). One observed consequence of the LDL reduction via apheresis both with and without adjunctive lipid-lowering pharmaceutical therapy has been the reduction of the incidence of restenosis after revascularization as well as a reduction of coronary events.

B. Autoimmune Disorders

Apheresis means have been employed to treat various autoimmune disorders. Depending upon the disease itself, its clinical manifestations, and the underlying mechanism of action, apheresis systems have been effective either as primary or adjunctive therapies. Some examples are listed below:

1) Lupus Erythematosis

Standard treatment of Lupus Erythematosis consists of corticosteroids and immunosuppressive drugs. Plasmapheresis has been shown to impart additional benefit to patients suffering from Lupus Erythematosis when used alone to treat acute symptoms or prior to immunosuppressive therapy (Euler et al., (1996) Transfius. Sci. 17, 245–265). The apheresis methods are employed to remove circulating antibodies, immune complexes and antigens that contribute to the etiology and/or progression of the disease.

2) Rheumatoid Arthritis

Apheresis has also been used to treat rheumatoid arthritis, a chronic and debilitating autoimmune disease which leads to inflammation and deformity of the joints (U.S. Pat. No. 5,782,792). The standard treatment involves weekly outpatient apheresis sessions utilizing a column containing Protein A immobilized on an inert silica matrix for 10 to 12 treatments. The Protein A binds to and removes antibodies, immune complexes and antigens that contribute to the symptoms of rheumatoid arthritis. A similar method has also been described for treatment of thrombotic thrombocytopenia purpura (U.S. Pat. No. 5,733,254).

C. Cryoglobulinemia

Patients diagnosed with cryoglobulinemia have been treated using various apheresis methods with successful results (Russo et al., (1996) Transfus. Sci. 17, 499–503; Siami et al., (1995) ASAIO J. 41, m315–m318). The final results of these studies indicated that treatment with apheresis resulted in a reduction in plasma viscosity and subsequent improvement in rheology and in the function of affected organs.

D. Age-related Macular Degeneration

Age-related macular degeneration (AMD) is a chronic, progressive, degenerative eye disease of unknown etiology. AMD is characterized by progressive loss of central vision, and is the most common cause of legal blindness in patients over age 65 in the industrialized world. Over fifteen million Americans are currently estimated to be diagnosed with signs and symptoms of AMD, most commonly in persons aged 65 and older, with over one and a half million rendered legally blind and nearly two million new cases being diagnosed annually. AMD is divided into "Dry" and "Wet" forms depending upon the morphological characteristics associated with the observed eye pathology.

Recently, Allikmets and others presented landmark research that implicates a defective gene in the pathogenesis of AMD (Allikmets et al., (1997) Science 277, 1805–1807). The gene, which is located at the 1p21 locus, codes for the manufacture of the ATP Binding Cassette transporter retina-specific (ABCR) protein. This superfamily of proteins is believed to be responsible for energy-dependent transport of various substances across retinal membranes, thus promoting the clearance of the retina's waste by-products of vision. In both rod and cone outer segments, hundreds of pigment disks are shed into the retinal pigment epithelial layer (RPE) of the retina daily. There the RPE cells phagocytize the pigment disk material, preparing it for transport across Bruch's membrane to be removed by the adjacent choriocapillary blood supply.

The reported genetic defect in AMD renders this waste removal pipeline less effective, allowing accumulations of debris to collect in the posterior retina at the layer of the RPE/Bruch's complex. When clinically evident, this debris is believed to collect in deposits termed drusen or basilar laminar deposits, depending upon the location of the deposit. It is believed that these deposits are directly toxic to surrounding retinal tissues, and that they may play a role in the progression of AMD. If so, depletion and/or removal of these deposits is hypothesized to have a beneficial effect on a patient's vision. Current research attempts to improve patients' vision by laser applications to these drusen deposits have been disappointing.

Other recent research supports the notion that AMD is concurrently associated with a dysfunction of the microcirculation in the posterior retina (Freidman et al., (1997) Am. J. Ophthalmol. 124, 677–682; and Grunwald et al., (1986) Ophthalmology 93, 590–595).

This body of research has repeatedly documented decreases in retinal blood flow, impaired choriocapillary perfusion, increased vascular resistance, and pulsatility, along with decreased blood volume and various morphopathologic changes in the retinal capillary vessels themselves. Although the precise etiology and mechanism of action for the occurrence of these changes are not yet understood, it is believed that AMD is promoted through a complex interaction of multiple etiologies. Therefore, until now, other than laser photocoagulation, there has been no therapy widely recognized to be effective and therefore commonly recommended for the treatment of this disease, and most certainly in its early "dry" stages.

Brunner, Berrouschot and others have documented that subsequent to MDF apheresis, reduction of rheologic factors induces numerous clinically evident rheological changes, including reduction of both whole blood and plasma viscosities, reduction of red blood cell aggregation, promotion of capillary blood flow, and enhancement of intrinsic endothelial cell function (Brunner et al., (1995) Intl. J. Artif. Organs 18, 794–798; Brunner et al., (1991) JAMA 18, 63–65; Brunner et al., (1996) Transfus. Sci. 17, 493–498; Widder et al., Invest. Ophthalmol. Vis. Sci. 38, s1-1176; Berrouschot et al., (1998) Acta. Neurol. Scand. 97, 126–130). These prior studies, however, failed to optimize timing intervals associated with apheresis treatments and therefore were unable to demonstrate maximal improvement in clinical outcomes. Specifically, the AMD study utilized a monthly interval between individual apheresis treatment cycles of two session which was insufficient to maintain reduced levels of RAMs. The ischemic stroke study utilized a protocol in which apheresis treatment was not given until six or more hours following stroke. The apheresis treatment protocol was also considered to be unsatisfactory because of the extended period of time prior to treatment (six hours).

E. Cancer

Other researchers have discovered and used a selective form of apheresis designated UltraPheresis™ as an innovative approach for the treatment of cancer (U.S. Pat. No. 4,708,713 issued to Rigdon Lentz). UltraPheresis™ removes a low molecular weight fraction of the blood containing immunosuppressive components, known as tumor necrosis factor (TNF-alpha) soluble receptors, from the blood of the cancer patient. When TNF-alpha receptors are removed, a patient's natural killer cell activity increases and is better able to recognize and attack the malignant tissue. UltraPheresis™ therapy thus is intended to stimulate the natural immune response that is suppressed by malignant tissue expression of tumor recognition suppressive agents. UltraPheresis™ can be distinguished from Rheopheresis® blood filtration because the former seeks to target the depletion of a specific small molecular weight fraction (less than 100 kDa) from the patient whereas the latter depletes the entire bandwidth of the high molecular weight fraction (greater than 500 kDa).

F. Renal Diseases

Apheresis has been shown to be an effective method for the treatment of many types of renal diseases including glomerulonephritis, glomerulosclerosis, nephrotic syndrome and many others as well. (Harada et al., (1 998) Ther. Apher. 2:193–198). However, the present invention is the first to contemplate the simultaneous use with dialysis for the secondary prevention and prophylaxis of the vascular complications associated with hemodialysis treatment.

G. Acute Coronary Syndromes. Brain Stroke and other Vascular Diseases

The utility of various apheresis methods in the treatment of various vascular diseases is currently under investigation. While the precise mechanisms of atheroma development have not been entirely defined, the most recent consensus states that atherosclerotic lesions develop as the result of biochemical cascades initiated in the presence of increasing plasma concentrations of certain lipids, proteins and other macromolecules that promote accumulations of proteaceous lipid-laden plaques within certain arterial walls. If these plaques rupture and lead to thrombosis and occlusion in the heart, this is called a heart attack, in the brain, this is called a stroke, in the limb this blood clot may lead to gangrene and amputation. Aneurysmal ruptures may follow a similar progression.

Apheresis methods, and membrane differential filters, like the RheoFilter™ MDF system in particular, have demonstrated their ability to remove circulating plasma macromolecules that have been implicated in capillary (endothelial) dysfunction, atherogenesis and thrombosis. The mechanisms are complex but likely include alterations of rheologic factors promoting synergies of: decreasing plasma viscosity, decreasing whole blood viscosity, decreasing erythrocyte aggregation, increasing shear stress and enhancing intrinsic endothelial cell function. Membrane differential filtration achieves these objectives, primarily through reductions of circulating macromolecules, especially the RAMs within minutes to hours.

For apheresis applications involving the treatment of vascular diseases, the ability to remove RAMs is of utmost importance. Recent research has demonstrated that fibrinogen, LDL, C-reactive protein, lipoprotein A and other circulating macromolecules have been associated as independent risk factors for the development of vascular disease. As described above, these moieties appear to have the ability to act both as acute phase reactants as well as chronic procoagulant modifiers. In addition, these molecules have been documented to precipitate and/or exacerbate the majority of endothelial injury response, vascular smooth muscle cell proliferation and modify extracellular matrix processes and integrated mechanisms associated with acute vascular events as well as participate in "oxidative stress" and "carbonyl stress" that up-regulate vascular injury on the molecular level. The MDF system of the present invention is able to suppress this overreaction by depleting the wide range of molecular substrate reactants consumed by the biochemical maelstrom that occurs acutely in such disease states and to maintain such therapeutic reductions for an extended period of time.

In the context of secondary prevention and/or acute vascular event management, truly effective interventional technologies must be able to rapidly and substantially eliminate the broad spectrum of molecular pathogenic factors that have been implicated in the injury response cascades described above. Whether such interventions are pharmacological ('statins') or physiologic (apheresis), they must at once preserve those components necessary for cellular repair and healing (i.e. cytokines, signaling integrins and other, typically low molecular weight proteins), while at the same time they must substantially deplete the compounds responsible for injury ("vascular injury risk factors"). This mandate represents the fundamental challenge of vascular disease management at present, especially given the time-to-effective-treatment requirements.

The present invention, preferably utilizing one of the RheoFilter™ MDF systems, rapidly and efficiently depletes those circulating macromolecules larger than 250 Å or about 500 kDa in weight and heavier. These include; most isoforms of LDL-C, LDL-ox, fibrinogen, IgM, alpha-2 macroglobulin, lipoprotein A, apolipoprotein B, von Willebrand factor, vitronectin and many others identified as potential risk factors in vascular diseases. Recent studies have demonstrated that depletion of any one of these plasma components may improve endothelial cell function, increase blood flow, improve clinical outcomes or promote significant decreases in the morbidity and mortality associated with the management of acute coronary and other vascular events and their sequelae.

Other forms of apheresis for vascular intervention: In the quest for improved outcomes beyond drug therapy alone, four LDL apheresis technologies (dextran sulfate adsorption (Kaneka, Liposorber, Japan), antibody immunoadsorption (Baxter, Therasorb, Germany), Lp(a) immunoadsorption (Lipopak, Pocard, Russia) and heparin precipitation (HELP® System, Braun, Germany)) have recently been introduced for the treatment of familial hyperlipidemias (elevated LDL cholesterol). As expected, each of these technologies demonstrates a modest incremental ability to reverse arterial plaque formation, improve blood flow and increase exercise tolerance in some patients. However, the high costs and technical complexities associated with these methods have precluded them thus far as widely accepted options in those markets currently addressed by pharmaceutical and dietary interventions.

However, the principle reason for the lack of general acceptance is that the technologies are considerably too specific (removing LDL almost exclusively) to be of substantial benefit in moderating the majority of the mechanisms associated with acute vascular injury response/reperfusion damage. The HELP® system is only slightly better than the others in that it additionally depletes fibrinogen and some lipoprotein A (Lp(a)). The Lipopak system is far better at removing Lp(a) than any of the others, but each fails to deplete alpha-2 macroglobulin, IgM, IgA multimers, fibronectin, von Willebrand Factor, C-reactive protein, and many other of the macromolecules documented to be integral in the vascular damage cascades. This is in stark contrast to the actions of the RheoFilter® MDF systems.

5. Apheresis Treatment Facilities
A. In-Patient Medical Center Setting

Generally, the setting for therapeutic apheresis methods has been reserved for the hospital environment treating gravely ill patients with acute life-threatening diseases or recurrent exacerbations of such diseases. This has primarily been due to the severity of the patients being treated and subsequently the reimbursement available for treatment. However, the current overhead expense of the hospital environment adds significant costs to these procedures that need not necessarily be applied to apheresis treatments for relatively clinically stable yet chronically ill patients.

Historically, physicians are not trained in providing apheresis treatments outside of the hospital environment and remain unaware that apheresis methods can be applied to treat chronic, age-related, degenerative, inflammatory diseases; with AMD serving as the prototypical example in any setting outside of the hospital. Similarly, most patients with such diseases are not aware that they have a condition potentially treatable with the apheresis methods described herein or that such a potentially beneficial apheresis treatment option exists in such out-patient settings.

B. Out-patient "Office" Setting

1. Rigdon Lentz UltraPheresis™ center

Outpatient plasmapheresis therapy has been employed for removing low molecular weight proteins for the treatment of certain forms of solid tumors (Lentz, (1 999) Ther. Apher. 3, 40–49). This outpatient clinic practices a selective form of plasmapheresis known as UltraPheresis™. This form of apheresis is more complicated and more expensive than Rheopheresis® blood filtration as described herein.

Specifically, it removes TNF-alpha receptors, a particular low molecular weight fraction (55–75 kDa) from a cancer patient's plasma as opposed to a high molecular weight fraction (i.e., greater than 500 kDa).

2. LDL apheresis treatment

One possible exception to the exclusive use of hospital or in-patient treatment settings involves the recent introduction of the use of LDL apheresis as a treatment for patients with clinically evident, refractory, drug resistant, Type II Familial Hypercholesterolemia - a chronic, slowly progressive, ultimately fatal illness. Currently, for reimbursement purposes, LDL patients obtain their treatment in hospital settings located away from their medical provider. These settings remain unmodified for the specific needs of these patients. In Europe, out-patient LDL apheresis clinics are used specifically for lipid lowering in select hyperlipidemic patients, however, these facilities are not designed to moderate rheologic diseases, nor are they disease specific clinics. Neither are the treatments provided systematized to be deliverable within an average physician's office where the "point of sale" use can be made to conveniently provide the most patients with the broadest available apheresis treatment options, at the lowest possible costs.

SUMMARY OF THE INVENTION

The present invention generally relates to therapeutic methods that involve the depletion of at least two species of Theologically active macromolecules from a patient's plasma. Preferably, such macromolecules are depleted for a period of time and to a level that is effective to produce an improvement in a measurable endpoint or clinical improvement in a disease associated with relatively elevated levels of rheologically active macromolecules. The invention also relates to methods involving either the direct or indirect depletion of other plasma constituents of the high molecular weight fraction of plasma, and/or those constituents responsible for or supportive of those atherogenic, thrombotic and/or inflammatory cascades as described herein.

More specifically, the invention relates to methods in which the depleted rheologically active macromolecules (or high molecular weight fraction of plasma constituents) include cholesterol isoforms (VLDL, LDL and IDL), triglycerides, fibrinogen, alpha-2 macroglobulin tetramers, IgM, Lipoprotein A, fibronectin, vitronectin, and IgA. Preferably the depleted plasma constituents (or high molecular weight fraction) have a molecular weight greater than about 500,000 Daltons, or, such constituents (or macromolecules in such fraction) have an average size for a biologically active isoform that is greater than about 200 Å across the shortest diameter.

In a preferred embodiment, the depleted components are depleted to a level of at least about 50% of their levels in the patient compared to that prior to treatment. In an alternative preferred embodiment, the volume of plasma processed in a single treatment session ranges between about 80% and 120% of the patient's total plasma volume. It is contemplated that such depletion may be accomplished by Rheopheresis® blood filtration, preferably using one of the series of RheoFilter® hollow fiber membranes. Generally, the time interval between successive Rheopheresis® blood filtration treatments ranges from about one day to about ten days and the total plasma volume processed in any one week period is at least about 200% of a patient's total plasma volume, and that the successive treatment interval prior to the next dual session preferably is about 16 days± about 3 days.

It is contemplated that such therapeutic methods will be effective to produce in the patient one or more responses, such as: (1) increased microperfusion or capillary function; (2) improved immune response; or (3) extraction of tissue-bound RAM and to deplete the extracted RAM from the patient's plasma. Such methods generally will be effective to produce in the patient a clinically observable improvement in a disorder characterized by elevated plasma levels of rheologically active macromolecules. Such disorders include: (1) age-related macular degeneration; (2) atherosclerosis; (3) rheumatoid arthritis; (4) autoimmune diseases; (5) Diabetes; (6) Alzheimer's disease; (7) Procoagulant states, and (8) neurodegenerative diseases.

In another embodiment of the invention, Rheopheresis® blood filtration filters are provided in a form in which they are packaged together with a label or package insert (or the like) indicating its use for treatment of an age-related, degenerative or inflammatory disorder characterized by elevated plasma levels of Theologically active macromolecules, or any of the foregoing disorders.

The present invention also encompasses diagnostic methods that involve the measurement of the absolute or relative amounts of at least two rheologically active macromolecules depleted from a patient's plasma by Rheopheresis® blood filtration. In particular, such methods involve making an assessment of plasma levels or rate of decrease of such levels post treatment, then making an assessment of the concomitant increase of the plasma levels of the depleted Theologically active macromolecules as they re-equilibrate toward pre-treatment levels. Patients are typically considered to have elevated levels if they are in the upper tertile or even more preferably in the upper quartile of ranges measured for human patients. In these settings, patients with elevations of certain of these macromolecules are generally considered to be "at risk" or exhibiting a "procoagulant state".

In a related aspect, the invention relates to methods of providing Rheopheresis® blood filtration treatment. The steps of such methods preferably include: (a) evaluating a candidate patient to identify whether the patient has a RAM associated disease and to determine that state and extent of that disease; (b) determining whether the patient exhibits elevated plasma levels of at least two RAMs; (c) declining to treat patients with Rheopheresis® blood filtration who are not likely to respond to treatment or who might be harmed by the treatment; (d) selecting a particular Rheopheresis® blood filtration treatment protocol appropriate for chronic versus acute medical situations; and (e) providing Rheopheresis® blood filtration treatment. Optionally, the step of selecting a particular Rheopheresis® blood filtration treatment protocol includes an evaluation of a data base containing data on other patients treated by Rheopheresis® blood filtration. Preferably, an additional step is the providing of disease-specific medical follow-up evaluations. The step of submitting data on the patient to a data base containing data on other patients treated by Rheopheresis® blood filtration also is contemplated.

In another aspect, the invention relates to an integrated apheresis treatment process including the steps of: (a) providing at least one dedicated out-patient, non-hospital, apheresis treatment facility; (b) locating and selecting ambulatory, community-dwelling patients potentially capable of benefiting from apheresis treatments within a community that can be served by said apheresis facility; (c) identifying and selecting from among said patients, by means which include measurement of serum levels of circulating rheologically active macromolecules in said patients, a subset of patients capable of benefiting from apheresis treatments; (d) performing apheresis treatments in sessions on the selected patients in said dedicated out-patient apheresis treatment facility; and (e) determining clinical endpoints to said apheresis treatments based upon reductions in serum levels of said theologically active macromolecules and correlations of clinical symptomatology through disease-specific testing and serial endpoint and clinical assessments.

In yet a further embodiment, the present invention relates to an apheresis treatment method, that includes the steps of: (a) identifying chronically ill patients having age-related, degenerative or inflammatory diseases, the chronically ill patients being considered candidates for an apheresis procedure; (b) storing patient profile data for the patient; (c) analyzing qualifying data for the chronically ill patient to determine applicability of an apheresis treatment; and (d) performing apheresis treatments in sessions on the chronically ill patient. Optionally, the storing step includes the storing at least one of medical history data, physical characteristic data, medical condition data, diagnosis data, historical procedure data, and clinical effect data. Also, optionally, the step of analyzing specifically includes one or more of these data elements: medical history, disease specific history, physical examination and interview data. Such analysis steps may also include comparing patient profile data with a composite patient profile that is generated using data from similar patients who have completed an analysis steps may also include comparing patient profile data with a composite patient profile that is generated using data from similar patients who have completed an apheresis treatment process, or the determining of at least one or more of the probability of apheresis treatment success, a potential degree of anticipated clinical outcomes based upon statistical nomograms from an analysis of historical composite patient profiles, and a most appropriate initial apheresis treatment protocol.

Another embodiment of the invention provides an apheresis treatment qualification method, including the steps of: (a) identifying a chronically ill patient having an age-related, degenerative, atherogenic, thrombotic or inflammatory disease, said chronically ill patient being considered a candidate for an apheresis procedure; (b) storing patient profile data for said identified chronically ill patient; (c) receiving, from a centralized database system, a composite patient profile derived from other patients similarly situated to said identified chronically ill patient; (d) comparing said patient profile data with said received composite patient profile; and (e) determining based upon the comparison in step (d), whether said identified chronically ill patient would likely benefit from apheresis treatments. Optionally the storing step includes the storing of one or more of the patient's medical history data, physical characteristic data, medical condition data, diagnosis data, historical procedure data, and clinical effect data.

The present invention also provides a method of screening patients for a Rheopheresis® blood filtration treatment. Such method includes: (a) identifying whether the patient has a RAM associated disease and determining that state and extent of that disease; (b) determining whether the patient exhibits elevated plasma levels of at least two RAMs; (c) selecting patients who are likely to respond to Rheopheresis® blood filtration treatment or who will not be harmed by the treatment; and, optionally, (d) selecting a particular Rheopheresis® blood filtration treatment appropriate for treating a specific RAM associated disease. The method may include the screening of a data base containing patient data from individuals treated by Rheopheresis® blood filtration to determine the most appropriate treatment protocol. In connection with that method, may be an additional step of submitting data in a patient profile to a data base containing patient data from other Rheopheresis® blood filtration treatment patients.

Yet another related aspect of the present invention is a treatment protocol generator for use in a system that endeavors to generate disease specific treatment protocols based on a patient profile. Preferably this treatment protocol generator comprises: (a) a treatment protocol derivation means for analyzing disease specific historical composite patient profiles to derive treatment protocols having enhanced therapeutic effect(s); (b) an identifying means for identifying particular data of a patient profile which will serve to optimize the disease specific apheresis treatment; and (c) a treatment protocol generating means for generating treatment protocol that, when executed, will enable optimization of the therapeutic effect of apheresis treatment. Such treatment protocol generators also may include: (a) a comparing means for comparing said data of said patient profile against a prescribed set of data to identify any of the treatment protocols substantially conforming to desired therapeutic result; and (b) classifying means for classifying the identified suitable treatment protocols in order of suitability based on the patient profile.

The identifying means of such a treatment protocol generator may include means for identifying, in accordance with said composite historical patient profiles, data from the database that will result a treatment protocol predicted to have a superior therapeutic effect. Preferably the data includes at least one of medical history data, physical characteristic data, medical condition data, diagnosis data, historical procedure data, clinical effect data, disease specific history data, physical examination data, and interview data. Also, preferably, the treatment protocol generator further includes an optimal set selecting means for selecting an optimal set of treatment parameters based on at least one of the following factors: (i) their respective predicted abilities to exhibit therapeutic results more closely matching the prescribed set of therapeutic results as indicated by said composite historical patient profiles; (ii) their respective predicted abilities to validate said composite historical patient profiles; (iii) their respective predicted abilities to discriminate between said composite historical patient profiles; (iv) their respective predicted abilities to induce superior therapeutic response; and (v) similarity between their disease specific characteristics and those in composite historical patient profile database whose therapeutic response most closely conform to the desired therapeutic response. The protocol generator also may include a means for selecting the optimal set by individually ranking the treatment parameters based on at least one of factors (i)–(v) or combinations thereof.

The present invention also provides an apheresis treatment data collection and treatment system, comprising: (a) a plurality of interconnected computer systems located at a respective plurality of apheresis treatment sites, said plurality of interconnected computer systems being configured to receive input reflective of apheresis treatment parameters and clinical effects produced by apheresis treatments, wherein at least one of said plurality of interconnected computer systems is located at a dedicated out-patient apheresis treatment facility; and (b) a centralized database system including a storage facility that stores apheresis treatment parameter data and clinical effects data that are received from said plurality of interconnected computer systems, said centralized database system further including a means for creating a composite patient profile based upon apheresis treatment data that is collected for patients treated at said plurality of apheresis treatment sites. Optionally, the plurality of interconnected computer systems and the centralized database system are interconnected to form a computer network and may also be connected to the Internet.

A related aspect of the invention provides methods for storing and processing input reflective of apheresis treatment parameters and clinical effects produced by apheresis treatments in a apheresis treatment data collection and treatment system, said method comprising the steps of: (a) configuring a plurality of interconnected computer systems located at a respective plurality of apheresis treatment sites to receive input reflective of apheresis treatment parameters and clinical effects produced by apheresis treatments, wherein at least one of said plurality of interconnected computer systems is located at a dedicated out-patient apheresis treatment facility; and (b) storing apheresis treatment parameter data and clinical effects data that are received from said plurality of interconnected computer systems in a centralized database system, said centralized database system further including a means for creating a composite patient profile based upon apheresis treatment data that is collected for patients treated at said plurality of apheresis treatment sites.

A further and related aspect of the invention involves an apheresis treatment data collection and treatment system. Such a system includes: (a) first means for enabling a user to enter information about a patient in a computer database; (b) second means for creating a summary of the information entered into the local computer database; (c) third means for periodically transmitting the summarized information to a data management system database; (d) fourth means for allowing local users to search the data management system database for a specific patient profile; (e) fifth means for performing data aggregation and analysis on the data management system database and for producing reports based on a search criterion; and (f) sixth means for allowing the local users to download the produced reports. Preferably, the sixth means for allowing enables licensed users to establish the efficacy of RheoThera®, Rheopheresis, VasoTherapy, AngioTherapy and like apheresis means.

DETAILED DESCRIPTION OF THE PREFERRED EMBODIMENT

1. General Description

Figure 1:
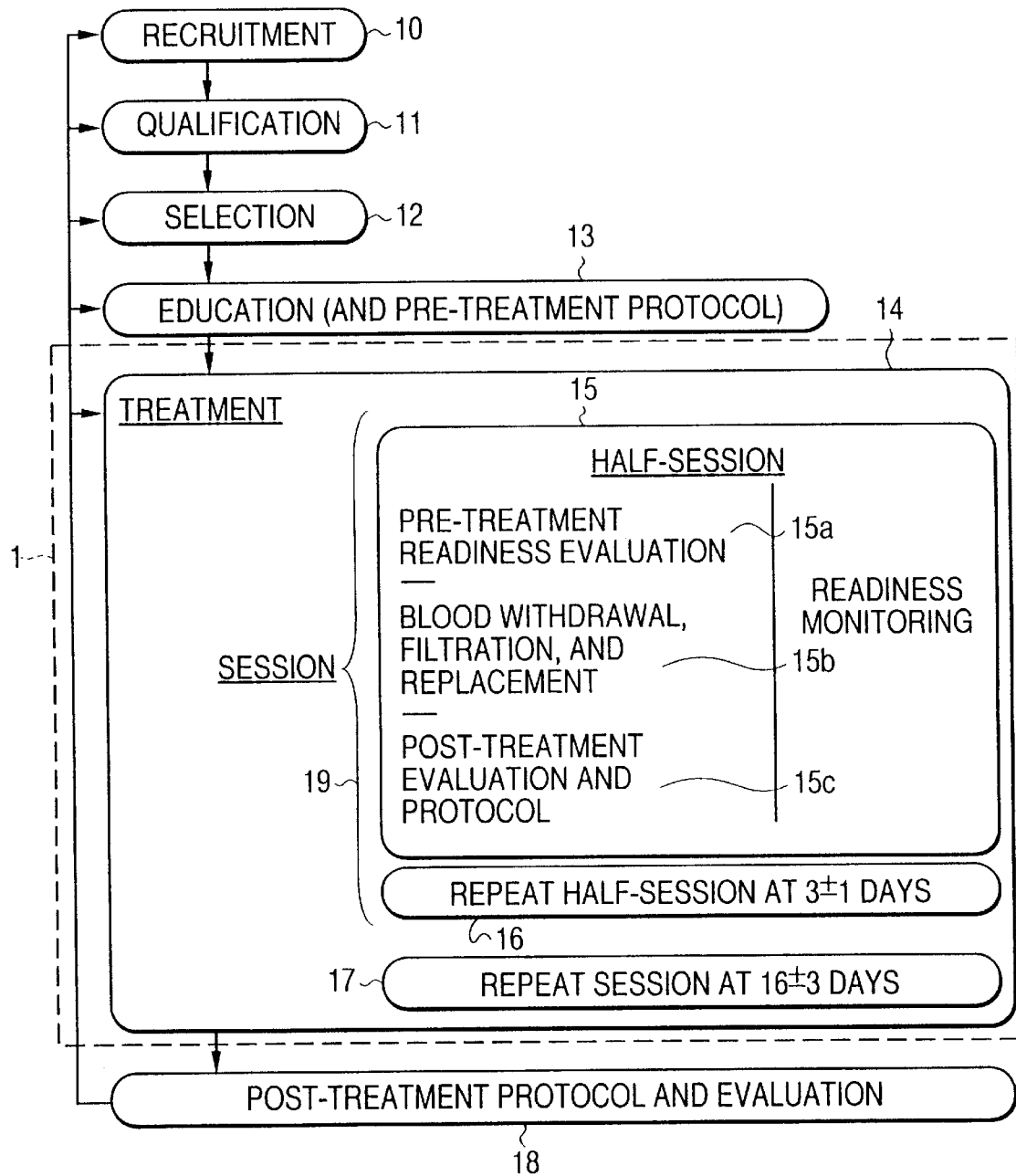
FIG. 1 is a patient interaction flow chart schematically illustrating progress of a patient going through a preferred embodiment of an apheresis treatment process.

The present invention relates to methods and apparatus for the therapeutic, simultaneous depletion of numerous high molecular weight components, particularly rheologically active macromolecules (or "RAMs") from a patient's plasmna. Such theologically active macromolecules are associated with a variety of pathological changes which include, for example, disruptions in microcirculation in affected tissues. RAMs characteristically exist in several isoforms, have numerous physiologic actions and are capable of promoting the expression of cell-cell receptors and adhesion molecules. Aside from their primary role in establishing blood rheology, they also tend to act as procoagulant molecules and can exhibit behavior like acute phase reactants in the setting of vascular injury as well. Elevated serum levels of certain of RAMs have been documented to: (1) cause increases in whole blood and plasma viscosities; (2) promote cell-cell adhesion; (3) disrupt intrinsic endothelial cell fimctions, and (4) cause numerous other pathologies which can promote various disturbances in the microcirculation measured as decreases in capillary perfusion leading to ultimate end-organ dysfunction or outright failure.

The methods and apparatus of the present invention utilize membrane differential filtration, and preferably a Rheopheresis® blood filtration process. However, regardless of the particular methods and apparatus utilized, the object of the present invention is the rapid, selective depletion or removal of a broad bandwidth of plasma components of high molecular weight, particularly rheologically active macromolecules. Certain of such macromolecules are known to be involved, directly or indirectly, in various diseases or disorders. However, all of the rheologically active macromolecules that circulate as high molecular weight plasma constituents have not yet been identified or linked to particular diseases or disorders. Preferably, at least two, three, four or five or more of the rheologically active macromolecules are removed or depleted according to the methods of the present invention. The methods and apparatus of the present invention generally are effective to deplete or remove such macromolecules and components as a class. Thus, levels of known high molecular weight plasma constituents continue to serve as markers for levels of presently unidentified or uncharacterized Theologically active macromolecules and components.

The general steps involved in Rheopheresis® blood filtration involve: (1) treating a patient by the extracorporeal circulation of the patient's blood, (2) separating first the cellular components from the whole blood, (3) directing the plasma components fraction thereof to a next filter, (4) sieving the plasma components to remove rheologically active macromolecules therefrom, (5) combining the RAM-depleted plasma with the patient's cellular components to reconstitute the patient's whole blood, and (6) returning the reconstituted whole blood to the patient's body in a continuous fashion in a sterile closed circuit. The particular equipment and apparatus utilized and the particular steps, for example, in returning blood components to a patient are not so important as the depletion or removal of the high molecular weight components of the plasma and the safe return of the remaining blood and blood components to the patient.

Preferably, such a procedure will be available for use in an average physician's in-office practice as a standard therapeutic modality. More preferably, such procedures will be conducted in a manner that accesses data from central data repositories in order to evaluate patients both as candidates for Rheopheresis® blood filtration and to provide prognostic information to the physician and to provide ongoing management advice to such a physician.

2. Definitions

"Community" means that group of subspecialists and their integral support staffs that provide similar medical services and treat subspecialty-related diseases, such as ophthalmologists treating eye diseases.

"Dedicated out-patient, non-hospital, apheresis treatment facility" means a physical facility that lies outside of a hospital setting designed to provide apheresis services to a specific disease group or medical subspecialty oriented activity.

"Depleting" means that the level of a plasma component, particularly Theologically active macromolecules, has been removed or reduced in a patient by treatment according to the present invention to a level that is below, and preferably substantially below, the level of that component in the patient prior to Rheopheresis® blood filtration treatment. More preferably, the therapeutic step of depleting such component(s) is effective to produce an improvement in a measurable endpoint or an observable clinical improvement in a disease or disorder associated with the presence of elevated levels of the plasma component(s) in that patient. In a specific embodiment of the present invention, the level of such plasma component(s), or of the rheologically active macromolecules as a class, has been reduced by at least about 35–50%, more preferably at least about 50 to 60%, even more preferably at least about 70%, and most preferably at least about 75% to 95% or more.

"Endpoints" means those quantitative and qualitative measurable events, tests, or other definable occurrences that constitute a variable for which statistical comparisons can be made at the conclusion of clinical study. By way of example, tests useful to measure such endpoints include the: (1) "BSCVA" which means best spectacle-corrected visual acuity; (2) "PVSRT" which means Pepper visual skills for reading test; and (3) "VF-14 score" which means a widely accepted standardized and validated test in the form of a subjective questionnaire designed to ascertain a patient's evaluation and subjective assessment of their low vision condition.

"High molecular weight fraction" means those plasma constituents having a molecular weight greater than about 500,000 Daltons or size of 200 Å diameter or more.

"Plasma constituents" or "plasma components" means those blood components in circulation either transported in, dissolved in or suspended in the serum fraction of whole blood.

"Plasma processing volume" means that volume, usually expressed in cc's, of blood or plasma that is circulated in the extracorporeal circuit during the course of an apheresis procedure.

"PTCA" —percutaneous translumenal coronary angioplasty, is a mechanical dilatation procedure whereby a balloon-tipped catheter is threaded through a narrowed vessel and inflated to expand the lumen and increase blood flow.

"Rheologically active macromolecules" or "RAMs" means high molecular weight proteins, lipoproteins and other proteinaceous moieties circulating in a patient's bloodstream that cause or are commonly associated with significant changes in blood rheology, extra-cellular matrix composition or endothelial cell function that may result in pathological changes in a patient. Such molecules are generally characterized as having one or more of the following characteristics: extracellular (located in interstitial space), hydrophilic, mobilizable, soluble in the normal plasma fraction and located within or immediately adjacent to a biologic semipermeable membrane that separates the material from a proximate blood supply.

"RAM accumulation-deposition diseases" means those disorders or diseases that are caused by or associated with elevated plasma levels of RAMs, and which typically involve the accumulation and deposition of such macromolecules. The terms "protein accumulation-deposition diseases" and "dysproteinemias" also have been historically applied to these conditions.

"Rheopheresis® blood filtration" means a specific extracorporeal blood filtration or apheresis process whereby a certain bandwidth of bloodstream constituents, such as the Theologically active macromolecules, are rapidly removed or substantially depleted through membrane differential filtration to remove high molecular weight plasma components. The filtration may also deplete tissue-bound deposits of RAMs. This filtration also modifies a patient's blood rheology in order to, among other things, change or improve the pathological state induced by or associated with the presence of the rheologically active macromolecules. Such changes may involve: (1) decreasing whole blood and plasma viscosities; (2) down-regulating cell-cell adhesion; (3) improving intrinsic endothelial cell functions, and (4) enhancing blood flow and perfusion in the microcirculation leading to improvement in end-organ function. As used herein, RheoThera® refers to medical procedures involving Rheopheresis® blood filtration.

"Type of rheologically active macromolecules" means an individual group or class of RAM, such as IgM, triglycerides, fibrinogen, etc.

II. Specific Embodiments

A. Rheologically Active Macromolecules

The human blood stream is replete with constituents that regulate both the hematologic, endothelial and rheologic homeostasis. Some examples of these molecules include:

Low Density Lipoprotein (LDL) cholesterols: These atherogenic lipoproteins are currently the subject of intense research. They include all of the LDL subclasses graded by particle size, lipid composition, and isoform structure. The latest means of measurement include nuclear magnetic resonance techniques (NMR), as well as enzyme-linked immunoselective assay (ELISA) techniques.

Triglycerides (TG): These high molecular weight lipids are another class of lipoprotein and are typically described as particle remnants given their dynamic metabolism after production in the liver and elsewhere. These molecular complexes are also measured by NMR and ELISA technologies.

Fibrinogen: This blood component protein is widely recognized as a potent risk factor of vascular disease and is involved primarily in the clotting cascade. As with other RAM, fibrinogen has numerous actions and can be rapidly converted to several forms including: fibrin-D dimers, Fibronectin and other byproducts and acute phase reactants. These molecular complexes are also measured by ELISA and precipitation technologies.

Alpha-2 macroglobulin (alpha-2 M) is a proteinase inhibitor whose primary biometabolic action is to regulate the production of plasmin. Rheologically, alpha-2 M is the most potent regulator of plasma viscosity gram for gram in human blood. It is measured by ELISA and gel electrophoresis techniques.

Lipoprotein A (Lp(a)) is a known cardiovascular risk factor. Lp(a) is a constituent of Apolipoprotein Al and serves as the primary ligand for the cholesterols. It is also measured by NMR and ELISA techniques.

B. Apheresis Equipment

Generally, apheresis equipment is comprised of an extracorporeal blood pump its constituent tubing and the filtering means. A preferred apparatus is the Plasmatic™ apheresis pump (Apheresis Technologies, Inc.), a three-function microprocessor controlled pumping device that embodies at least 4 roller blood pumps and the salient alarms, setting controls and monitors typical of such apheresis pumps. Secondarily, the Octo 2000® (Apheresis Technologies, Inc. USA; Mesas, GmbH, Germany) provides a multi-functional extracorporeal pumping station providing eight different settings to afford numerous configurations to provide all extracorporeal treatments except dialysis. The preferred filters in the methods and apparatus of the present invention are the Plasmaflo OP-05 (WL) and RheoFilter® AR 2000®, AR 4000® and AR 3000® (all manufactured by Asahi Medical Company, Ltd.). In addition, vascular access needles and various vital signs, blood and oxygen monitors are utilized during treatment as is standard in the in-patient apheresis setting.

C. Integrated Apheresis System

In one aspect, the present invention relates to an integrated, medical subspecialty-directed, disease-specific apheresis treatment system.

Freestanding Outpatient Apheresis Treatment Facility: One aspect of the apheresis treatment system of the present invention is to employ freestanding, dedicated, outpatient apheresis treatment facilities (or apheresis treatment centers) (see FIGS. 1 and 2) in a network (only one shown in FIG. 1) for providing apheresis treatment procedures to ambulatory patients with RAM accumulation-deposition diseases. Currently, apheresis procedures, where available, are generally carried out only in hospital settings, in large part due to the historic reimbursement guidelines and the requirement for proximate advanced life support means necessary for the appropriate medical treatment of acutely ill patients in need of apheresis treatment. By performing apheresis procedures on relatively stable chronically ill patients, the opportunity is afforded to provide those treatments to a broader patient base and to do so in a more cost-effective manner.

In addition, such a freestanding facility makes it possible to provide highly specialized and individualized treatment to every patient, while also providing easier access for the patient to obtain such medical care. Many chronically ill patients, especially low vision ophthalmologic patients, experience great difficulty in traveling even short distances, even to the point of not obtaining medical services due to the difficulty of undergoing such travel. Physically integrating such abovementioned apheresis treatment into such patients' physician's existing practice would provide maximum access to treatment and follow-up for such patients.

Finally, continued specialized experience in such a medical subspecialty-directed, disease-specific apheresis treatment network formed of freestanding apheresis treatment centers results in a more concentrated degree of expertise in the physicians, nurses, and other personnel involved in delivering and following up on the patients' clinical course as such pertains to the present invention. This is especially true in the assessment of patients' responses to treatment where the clinical outcomes to be determined are far more subtle than whether the patient merely survived the illness [treatment]. In one embodiment, the physician may be located off-site but will be immediately available by wireless communication, and the facility will provide a nurse practitioner, a nephrology nurse practitioner or registered nurse with sufficient supervisory experience.

Figure 2:
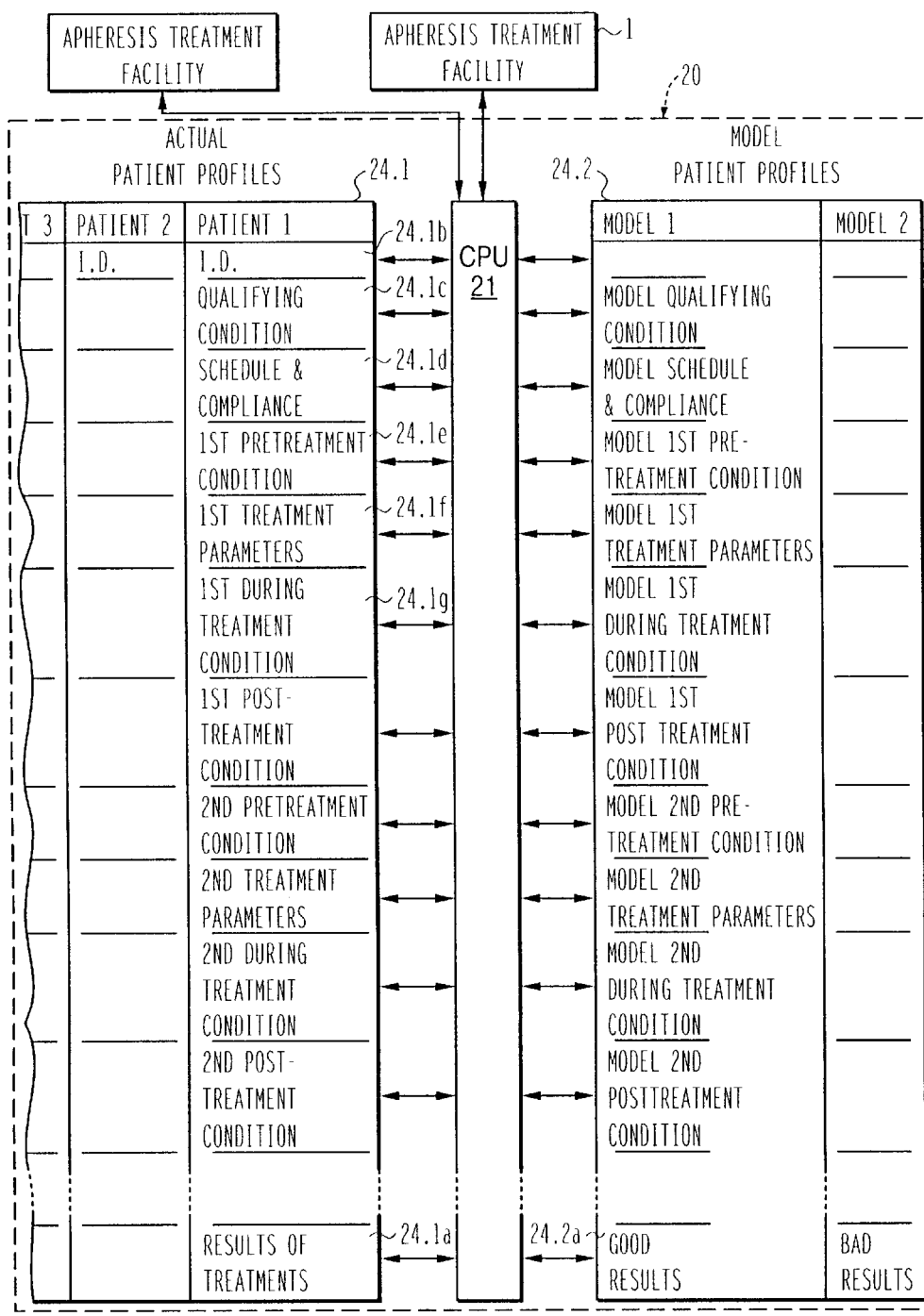
FIG. 2 is a continuous improvement flow chart schematically illustrating use of a preferred embodiment of an apheresis data processing network.

Although only two freestanding, dedicated, outpatient apheresis treatment facilities 1 are depicted in FIG. 2, it will be appreciated by those persons skilled in the art that there could actually be a large number of such facilities in the network distributed over a large area, even throughout a country, or globally for that matter. Preferably, such facilities are anticipated to be linked together in a secure, encrypted computerized medical database and outcomes analysis system as described herein for network and/or Internet distribution of said system-wide data in the preferred embodiment hereof.

Computerized Data Management System: The integrated apheresis treatment process, business delivery method and computer-linked network of this invention, preferably to be carried out over such an Internet platform, preferably utilizes a computerized data management subsystem 20 (FIG. 2), optimally comprising at least one computer, or CPU, 21 and a storage device 24 (actually shown in FIG. 2 as two separate storage devices—actual-patient-profile and composite-patient-profile storage devices 24.1 and 24.2—for ease of explanation) as well as all associated software required to manage and control the system. The computerized data management system can be located in one of the apheresis treatment facilities 1, but it need not be. In fact, in the preferred embodiment, such a data management system is centralized for ease of maintenance in a separate facility with specialized technicians dedicated to the continuous care and maintenance of the computer hardware, integration of updated software versions, network troubleshooting, and overall database system management. Therefore, In FIG. 2 the data management system is not represented as being inside a treatment facility 1 for preferred purposes hereof.

The data management system 20 provides the capability to: (1) track apheresis patients through contact, education, evaluation, selection, medical clearance, treatment, referral, and post-treatment evaluation and follow-up processes; (2) provide real-time paperless data entry of apheresis treatment parameters during apheresis procedures at the treatment facility; (3) provide central access for real-time remote monitoring via a secure Internet link of all steps in the apheresis treatment process in the network of freestanding facilities; (4) provide all authorized members of the network with the ability to enter patient data and to retrieve reports and analyses based on all prior patients treated (while maintaining the confidentiality of patients' identities) in the network including clinical outcomes, responses to treatment, treatment protocols used, safety analyses, duration of treatment effects, etc.; and (5) provide predictive statistical analyses for individual prospective patients.

The computer system's software architecture is coded in such a way that it can readily be expanded, even to include other diseases in addition to the AMD example given in the preferred embodiment herein. As will be readily appreciated by persons skilled in the art, such a system will be configured in such a way so as to be easily expandable to readily provide similar capabilities of similarly providing information on all apheresis treated patients with any of the diseases mentioned herein, but such a system is not necessarily limited to those diseases specifically cited, or necessarily for apheresis treated patients.

The present invention thus provides a computerized data processing system for coordinating, managing, directing, entering, accessing and analyzing all aspects of both local and remote medical subspecialty-directed, disease-specific apheresis services anticipated by the present invention throughout the network.

The computerized data processing system is designed to maintain patient records and to serve as a repository for pertinent patient data at both the local and Internet level. At the local level, licensed users may support a secure local database with patient information, retain patient charts, and access Web reports. At the Internet level, relevant data is stored in the database on a data management system for aggregation, analyses and reporting. Licensed users may access data in the data management system by creating reports and may implement further analysis of reported information to establish the efficacy of Rheopheresis®.

In a preferred embodiment, local users may input data into the data processing system, for each patient, on several transaction forms, which are accessed from a main switchboard in the data processing system. The main switchboard displays information about the system and a list bar, among others. The list bar is the primary means of navigating through the system. Users may click on icons in the main switchboard to open patient forms, locate patient records, transfer or download data to and from the database in the data management system and/or maintain system tables. After data has been entered into forms at a local site, the data is periodically uploaded to the database in the data management system by means of the Internet. Local users may retrieve reports from the local database and/or retrieve reports generated from the data aggregation and analysis that the system performs on the database in the data management system.

Specifically in a preferred embodiment of the invention, a user enters information about a patient at a computer in a local location. At a periodic predetermined time, a summary of the data, summarized by pre-selected data fields, is transmitted to the data management system's database. Thereafter, local users may search the data management system's database for a specific patient profile. Alternatively, local users may use the data management system database to research multiple patients' profiles. The data processing system performs data aggregation and analysis on the data management system database and produces reports. This enables local users to retrieve information about patients with similar profiles and maintain patients' confidentiality. The local users may then download the produced reports to establish the efficacy of rheotheraphy.

Referring to FIG. 2, this data processing, or managing, system optimally includes at least one computer (with operating redundancy), or CPU, 21 for processing data. The CPU 21 receives actual-patient data from the apheresis treatment facilities 1, as is further described herein, initializes and indexes this data and stores it in at least one actual-patient-profile storage device 24.1 in the form of profiles for actual patients. Although FIG. 2 shows multiple arrows extending between the CPU 21 and the actual-patient-profile storage device 24.1, one arrow for each type of data, this is done for illustrative purposes only, because the different types of data could also be e-mailed, scanned, or multiplexed, between these two components on fewer lines.

The CPU 21 is also capable of processing and analyzing data from the actual-patient profiles of all patients previously treated by the medical subspecialty-directed, disease-specific apheresis providers within the network, along with data from all patients currently undergoing treatment and creating therefrom composite-patient-profiles, which are shown in FIG. 2 as being stored in at least one composite-patient-profile storage device 24.2. It should be understood by those persons skilled in the art that the various storage devices shown herein could be single or numerous devices, combined in any convenient, or desired manner, however, they are shown separately here for purposes of illustration. It should also be noted from FIG. 2 that actual and composite patient profile processing also includes as part of each profile, the results 24.1a and 24.2a of the treatment, both for actual profiles 24.1a and composite profiles 24.2a located, generated and/or stored within the system.

Patient Recruitment: Referring to FIG. 1, a first step 10 in a treatment system, including an integrated medical subspecialty-directed, disease-specific apheresis treatment process and a business delivery method of the present invention, is to locate, primarily by advertising and by referrals from a treating physicians' referral network, ambulatory, community-dwelling patients with chronic, age-related, degenerative, atherogenic, thrombotic and/or inflammatory diseases, with AMD serving as the prototypical example. These would be patients who are capable of potentially obtaining clinical benefits from obtaining the disease-specific apheresis treatments described herein. Locating such ambulatory, community-dwelling patients with such diseases is difficult. It involves the use of numerous coordinated marketing methods, including: direct-to-patient mailings, advertising in various media such as television, radio, the Internet, and newspapers; and direct-to-physician marketing within the disease specialty (e.g., ophthalmologists and optometrists seeking to treat AMD patients) in various formats, such as attendance and speaking engagements at related medical specialty meetings and seminars and office visits of the referral network participants.

Preferably, such marketing activities are coordinated and administered as part of the routine business operations of a treating physician's established medical practice. A significant marketing effort therefore will be expended by the treating physician recruiting patients already within his or her practice. However, such activities need not be limited to the physician's existing patient practice population.

During this awareness/recruitment step 10 (see FIG. 1) as each potential patient is located, identifying data (name, social security number, age, condition, diagnoses, clinical symptoms, past medical history, etc.) for that patient is entered into the CPU 21 (see FIG. 2), which initializes it, indexes it and stores it at 24.1b as part of that patient's profile in the actual-patient-profile storage device 24.1.

It is therefore another object of the present invention to contemplate extensive marketing efforts to physicians within a pertinent subspecialty (e.g., ophthalmologists and optometrists seeking to treat AMD patients) to acquaint them with such an apheresis method, as described herein, as a possible therapeutic modality for their patients, and acquaint them with the apheresis means and methods, as described herein, as a convenient, cost-effective and profit making means for providing safe and effective therapy for such patients' conditions within the context of their existing medical practices.

The present invention contemplates the encouragement of physicians to obtain, from the operations of the business as described herein, the necessary knowledge and confidence to recommend such medical subspecialty-directed, disease-specific apheresis procedures to their patients. Or alternatively and preferably, to obtain, from the operations of the business as described herein, the necessary knowledge and confidence to establish such a medical subspecialty-directed, disease-specific apheresis treatment facility within their existing practices to provide such apheresis treatments to their patients as a profitable enterprise within the context of their own practices. The primary challenge of course in conducting such a business is to persuade such medical subspecialists (historically unequipped and uneducated as to providing disease-specific apheresis means and methods to their patients, e.g., ophthalmologists and optometrists in the case of patients with AMD), to provide such apheresis services to such patients.

Patient Qualification, Selection, Clearance and Education: In addition, with each recruited patient's informed consent, he/she is given a preliminary physical examination, preferably at one of the apheresis treatment facilities 1, as part of a qualification step 11. However, any qualified examiner armed with the specific treatment-qualifying specifications and other pertinent information as supplied by the apheresis provider could adequately perform such an examination.

(Similar activities are performed during pre-surgical examinations, which are provided by qualified vendors or contractors for surgeons performing various procedures.) Qualifying data from this preliminary physical examination is entered into the CPU 21, which, in turn, initializes it, indexes it and stores it in the actual-patient-profile storage device 24.1 at 24.1c as an additional part of that patient's actual profile. The qualifying data is initially used for purposes of qualifying that patient for undergoing medical subspecialty, disease-specific apheresis procedures of this invention. This qualifying data includes information which can be derived from such an initial medical evaluation, and will typically include such items as: (1) past medical history; (2) disease specific history; (3) comprehensive physical examination, including laboratory blood tests that may include CBC, clinical chemistries, rheology panel, coagulation profile, lipid profile, immunological profile, and possibly ancillary tests such as EKG, stress tests, renal function, and pulmonary function, etc. as appropriate, as well as information which can be derived from an interview. In addition, the laboratory analyses of pertinent hemorheologic parameters will receive unique and special attention since they will frequently be used as gating factors that will determine whether a patient shall undergo the apheresis treatment process or not.

Patient Qualification Analysis: At this point in the process, the apheresis provider will access the CPU 21 to analyze the actual patient's profile compared with a selectable composite patient profile. It will be understood by those skilled in the art that although the actual patient profile, at this point, is limited, or incomplete—because this prospective patient has not completed the entire process—the composite patient profiles were generated by the CPU 21 using data from similar patients who have completed the entire apheresis treatment process. The composite patient profiles are composites that have been iteratively generated by the CPU 21 compiled from all of the actual patient profiles, which have been previously generated and entered into the network's computer system.

These composite patient profiles are dynamic, in that they are continually changing being continuously updated by data entry by all network apheresis providers globally. In fact, the CPU 21 is configured in such a fashion such that it can analyze the data on an individualized basis each time they are needed and generate unique, real-time customized analyses on a patient-by-patient basis. The composite patient profiles include historical clinical outcomes and other pertinent results 24.2a, while the actual patient profile for a prospective patient who has just qualified for treatment does not yet include any results 24.1a. In any event, once the CPU 21 distills the composite patient profiles that substantially and favorably compare with the prospective patient's actual patient profile based upon selectable comparison factors entered by the apheresis provider, it can determine: (1) the probability of treatment success; (2) the potential degree of anticipated clinical outcomes based upon statistical normograms from an analysis of the historical patients' profiles of similar patients, and (3) determine the most appropriate initial treatment protocol for the individual prospective patient about to begin apheresis treatment.

For example, the CPU 21 can determine that: if 800 of 1000 previously-treated patients with substantially similar actual patient profiles were successfully treated and obtained a sufficiently successful clinical outcome while undergoing six apheresis treatments of a specific nature, then the prospective patient has an 80% chance of obtaining similar results using the specific six-treatment protocol. Using this information generated by the CPU 21, the patient in consultation with the apheresis practitioner in the apheresis treatment facility 1 can elect or not elect to undergo the procedure, at the selection step 12. Such a real-time prognosticating capability tool has never been available to medical practitioners before, and provides a significant amount of comfort and confidence to such medical subspecialists newly providing such apheresis treatments to their patients, despite the fact that they have heretofore been historically unequipped and uneducated as to providing disease-specific apheresis means and methods to any patients at all.

Patient Medical Clearance: More particularly, patients are qualified (or disqualified) and selected (or not selected) as candidates for treatment by apheresis treatment center staff who, using the data management subsystem 20, consider five areas: (1) past medical history; (2) disease specific history; (3) comprehensive physical examination, including blood laboratory tests that may include CBC, clinical chemistries, rheology panel, coagulation profile, lipid profile, immunological profile, and possibly ancillary tests such as EKG, stress tests, renal function, and pulmonary function as appropriate; (4) disease specific examination (e.g., ophthalmologic examination); and (5) historical outcomes of patients with similar profiles, to firmly establish both the accuracy of the diagnosis as well as the present extent of the disease process. Physical examinations and/or laboratory tests may be conducted on site, or may be performed by consultants or qualified off-site vendors to accomplish this objective, as mentioned above. However, the clinical decision to determine a patient's qualification and suitability for the apheresis treatment herein, under the preferred embodiment of this invention, is made by the apheresis treatment center's 1 medical staff, in consultation with the prospective patient, prior to the prospective patient undergoing treatment.

Consistency in and completeness of patient assessment and the consistent collection and review of high quality data are an important part of patient identification, evaluation, assessment and clearance for treatment in the integrated medical subspecialty-directed, disease-specific apheresis treatment process and business delivery method of this invention. Therefore, the CPU 21 network system is programmed with a number of routines and subroutines that will automatically alarm and identify data omissions and/or obviously erroneous data entries such that the system will accept only the most accurate and highest quality data at all times.

As illustrated in FIGS. 1 and 2, patient qualification at step 11, is based on overall physical condition, and patient selection at step 12, is based on the likelihood that the disease can be ameliorated. Such determinations are continuously improved by iterative feedback from post-treatment evaluation 18 of historical, composite patient profiles, and from further "completion" of the actual patient profile of the individual patient as he/she progresses though the multi-treatment apheresis process of the present invention.

Before selection, as well as during and after treatment, patients and their families require extensive education. This education is best performed individually and should cover all of the concerns of patients including extensive discussions concerning the sought-after benefits and potential risks of the apheresis treatment process. In a preferred embodiment herein, dedicated education nurses operating within the apheresis treatment center 1 provide such ongoing education to patients and their families. The educator initially provides patients with literature articles and reports of the present clinical experience. Later, the educator can use the CPU 21 to provide a printout of numerous aspects of the therapy, including an individualized report that can include the probability for improvement, safety profile and the potential degree of improvement as described herein. Also, all known potential complications and risks, as well as the benefits of the treatment are described in detail. Finally, prospective patients are provided with a tour of the apheresis treatment center to acquaint them with the entire process and to meet the staff. Patients are also given the opportunity to meet current patients to obtain their perspectives. Low vision patients are then read aloud an informed consent with their individualized treatment protocol to be signed in the presence of a witness. Only then is the prospective patient considered as a candidate for apheresis treatment.

Patient Pretreatment Preparation: One aspect of patient education that directly impacts and becomes part of the overall therapy relates to the pre-treatment patient preparation regimen. In the days prior to their first apheresis procedure session, a patient is encouraged to engage in light exercise, such as walking, swimming, mild aerobics, and the like, designed to improve his or her circulation. Also, the patient is counseled to cease smoking, and is encouraged to adopt a low fat diet, high in green leafy vegetables, the diet being supplemented with vitamins, anti-oxidants (e.g., especially the leutines and xeoxanthanes), minerals (zinc), herbs (e.g., bilberry) as directed by the educator.

In addition, patients are instructed in venous access preparation including applying serial hot packs to the access sites, ball squeezing techniques and other methods to improve the caliber of the veins, as well as the blood flow through them. Patients are instructed to eat a large meal shortly before obtaining their apheresis treatments. Finally, patients are also directed to withhold certain medications prior to the day of treatment. (This would not include, of course, such medications as insulin and anti-seizure medicine, and others as directed by the Medical Director of the apheresis center 1.)

Again, data related to these education steps, including diet, exercise, medications, etc. are fed into the CPU 21 by treatment center 1 staff, and the CPU 21, in turn, initializes it, indexes it and stores it in the actual-patient-profile storage device at 24.1*d* to become part of the patient's actual profile. Similarly, since this data was also stored for previous patients, thereby being incorporated into the historical composite patient profile, the newly updated actual patient's profile can be compared with the composite patient profiles to see how these steps (for example, exercise) affect the probability that the integrated treatment process and business method of this invention will be successful for this patient. Also, using this type of data, the treatment center 1 staff can tailor the education process to optimize the probability and the degree of success along with providing realistic expectations of treatment outcomes to the patient, his or her family, referring physicians and the apheresis staff alike.

Thus, as illustrated in FIG. 1, education 13 is continuously improved by iterative feedback from post-treatment evaluation 18.

The Apheresis Procedure: In the preferred embodiment herein, the apheresis-procedure step 14, and its substeps 15–17, as indicated in FIG. 1, is carried out in one of the apheresis treatment centers 1. An aspect of the apheresis-procedure step 14 is the design of an individualized regimen of apheresis treatment whose timing, duration, plasma processing volume and other specific treatment parameters are optimized for each patient at each treatment, and in which intra-treatment anticoagulation and monitoring is also optimized. Such a regimen, or protocol, is also entered into the CPU 21 and stored in the actual-patient-profile storage device 24.1 as part of the patient's profile at 24.1*d*.

As illustrated in FIG. 1, apheresis procedures according to one embodiment of this invention are each based on "half-sessions" 15 which are repeated optimally 1 to 4 days later to complete a full session 19. This (full) session is then optimally repeated again after a recovery interval of 16±3 days, and preferably about 10±3 days, until a post-treatment evaluation demonstrates significant leveling off of the treatment effect and/or sufficient amelioration of the symptoms of the disease state or other clinical endpoint has been achieved.

A half-session 15 includes sequentially: pretreatment readiness evaluation 15*a*, with the results thereof being stored in the actual-patient-profile storage device 24.1 at 24.1*e* as an additional part of the patient's actual patient profile; blood withdrawal, filtration, and replacement 15*b*, with parameters thereof being stored in the actual-patient-profile storage device 24.1 at 24.1*f* as an additional part of the patient's actual patient profile; and post-treatment evaluation and protocol 15*c*, with the results thereof being stored in the actual-patient-profile storage device 24.1 at 24.1*g* as an additional part of the patient's actual patient profile. A half-session 15 also includes continuous vital signs monitoring during the course of apheresis treatment, again, results thereof are stored in the actual-patient-profile storage device 24.1 as an additional part of the patient's actual patient profile. As is widely known by those skilled in the apheresis arts, such information on patients' responses and reactions to treatment is important due to the fact that individual patients have a highly variable tolerance to apheresis treatments. Subsequent apheresis treatments can be modified to provide patients with an improved experience when such historical information of responses to treatment is provided.

It should be noted that particular areas of the actual patient profile storage device referred to herein do not necessarily refer to position locations, although they are represented in this manner in the drawings to facilitate understanding. Each piece of data added to a patient's actual patient profile makes possible more refined instructions from the CPU 21 as to how best to proceed with any further treatments for a particular patient and as to predictions by the CPU 21 as to the likelihood of clinical improvement as well as the potential degree of clinical improvement for the patient. This information is available and becomes increasingly more accurate as the CPU 21 identifies composite patient profiles which yet more completely correspond to the data of the actual patient profile as the patient progresses though their treatment regimen.

A treatment protocol generator for use in a system that endeavors to generate disease specific treatment protocols based on a patient profile is also contemplated as an embodiment of the invention. The treatment protocol generator is comprised of a treatment protocol derivation means for analyzing disease specific historical composite patient profiles in order to derive treatment protocols having enhanced therapeutic effect, a means to identify particular data of a patient profile that will serve to optimize the disease specific apheresis treatment, and a treatment protocol generating means for generating a treatment protocol that, when executed, will enable optimization of the therapeutic effect of apheresis treatment.

Treatment Session Initiation and Interval Timing: One of the most critical elements of performing safe and effective serial apheresis treatment is the proper sequencing of serial treatments since excessive apheresis treatments can deplete essential blood elements and prolonged treatments may lose their clinical effect. Those blood elements that can be dangerously depleted by overly aggressive plasmapheresis include: the coagulation protein factors, albumin, calcium, hematocrit, and proteins regulating immune function. In practicing the apheresis methods of the present invention, it must be kept in mind that although older-aged patients are typically less resilient than younger patients, if properly selected as per the above criteria, they are generally in better overall condition from an apheresis point of view than those younger, but gravely ill patients historically requiring apheresis treatments. Therefore, the standard regimens historically developed for younger patients with different diseases are not necessarily applicable in the present situation of the present invention.

This is especially true of relatively clinically stable patients suffering from chronic, age-related, degenerative, atherogenic, thrombotic and/or inflammatory diseases including AMD, who require specialized, medical subspecialty-directed, disease-specific management by treatments that are planned and customized for each individual patient's unique needs, disease process, and clinical condition. Accordingly, apheresis treatment is conducted only after the pre-treatment readiness evaluation 15a is performed immediately prior to each treatment. This evaluation includes an abbreviated interim history a brief physical examination, and the evaluation of laboratory tests including calcium, ACT coagulation, hematocrit, and such other tests as may be suggested by patient's condition and previous response to treatment experience. In addition, prior to each treatment, patients are assessed for changes in weight, plasma volume, and state of hydration. These factors, as well as the patient's demonstrated tolerance to prior apheresis procedures, will factor into both the decision whether to proceed with apheresis treatment at all, and if so, what the target plasma volume percentage for that day's treatment will be. Again, this data is fed into the CPU 21 to become part of the patient's actual profile, and decisions as to how or if to proceed are based on the CPU's 21 comparison of this updated profile with the composite patient profiles. Of particular note, it is not the intention of the computer system of the present invention to supersede the clinical decision-making of the apheresis providers and medical staff of the facility 1. The computer system is provided to be merely an efficient tool, designed to assist clinicians in making the numerous determinations relating to the care and treatment of their patients. The ultimate decisions concerning the treatment of said patients herein, shall remain the exclusive domain and responsibility of the providers of the patient's care. Their clinical acumen and expertise will always provide the basis of any and all treatment-related decisions made.

Intra-treatment Evaluation and Monitoring: In a similar manner, continuous and careful evaluation of a patient's clinical symptomatology during the multi-treatment apheresis protocols guides the duration of the apheresis treatments for patients, again based on feedback from the CPU 21. The objective of any individual apheresis treatment of the present invention as it is applied to said patients herein, is to process 100% plus or minus 20% of such a patient's plasma volume, with 100% being considered the usual target, and about 200% being processed in any one week period of time. However, such a patient must remain clinically stable in the judgment of the apheresis provider, throughout the apheresis procedure in order to maintain the safety margins necessary to continue the procedure. Therefore, the preferred embodiment of the present invention provides for continuous measurement of pulse, blood pressure and oxygen saturation, and regular, intermittent measurement of temperature and respiration throughout the apheresis procedure and during one hour afterwards in a recovery monitoring environment. Adverse events in apheresis procedures are rare, but can occur. Continuous patient monitoring, combined with good clinical judgment offer the best means to provide said apheresis treatment described herein safely and effectively. Fortunately, the expression of adverse events typically evolve slowly and can be immediately halted and reversed with suspension of the treatment process.

D. Preferred Design of a Network System

A preferred network system is designed to maintain patient records and to serve as a repository for pertinent patient data at both the local and Internet level. This example illustrates the development of such a system related, for example, to the treatment of patients with ocular disease. At the local level, licensed users will be able to support a secure database for patient information, retain patient charts, and access web reports. Visual Basic will be used as a front end to a Jet Access backend. At the Internet level, relevant data will be stored in a central location using SQL for aggregation and reporting. Licensed users will have access to this data through the use of reporting. Licensed users may implement further analysis of report information to establish the efficacy of RheoTherapy®.

The system accomplishes these tasks by capturing data that the user inputs on several transaction forms for each patient. To access these forms, the user is presented with a Main Switchboard upon launching the application. The Main Switchboard displays information about the system and site licensee as well as a List Bar. The Main Switchboard has a similar look and intuitiveness as Microsoft Outlook or Outlook Express. The List Bar is the primary means of navigation throughout the system. Icons are exposed which the user clicks to open patient forms, locate patient records, transfer or download data or to maintain the system tables. The patient forms are the entry points for data storage. These forms are organized into eight categories that are displayed in a Tree View. The Tree View presents items in a hierarchical list resembling Microsoft Windows Explorer. Subcategories are located underneath the categories in an outline style to further enhance the ease of user interaction.

The form categories include General Patient Information, Medical Providers, Patient Check List, History & Physical, Ocular Information, Treatments, Lab Results and Documents. The comprehensive areas of History & Physical, Ocular Information, and Treatments have a series of forms associated with specific areas of importance for each category. After the data has been gathered at the local site, the information will be periodically uploaded to the central repository by means of the Internet. In addition to local database reports, users will be able to retrieve reports generated from the data aggregation and analysis that the system performs on the central database. Specific local reports include the Patient Treatment Summary Report and the Patient Response Report, local and Internet Reports will be the Overall Improvement Report, Period Summary Report, QI Report and an Internet only Patient Prognostication Report. The Patient Prognostication Report is further divided into Visual Acuity Assessment, Subjective Questionnaire Assessment and Objective Assessment.

Specifically, the General Patient Information form contains the patient's name and address as well as related information including the next of kin and emergency contracts. The patient information may be searched through the use of a Patient Finder. The finder examines the database for matches to searchable fields that the user is able to select from a list. Boolean operators such as greater than, less than, equal to, and between give the user greater flexibility to narrow the scope of their inquiry. Further selecting a Criteria to search field upon by using a single letter of the alphabet, the first few letters of a name, or a given date, for example, provides additional versatility for the user to quickly locate the specific information they are trying to retrieve.

The Medical Providers record contains the names of Family Physicians, Ophthalmologists, Optometrists, and others that have contributed to the patient's overall medical care as well as eye care. This is also a searchable set of records where the users can locate specific information regarding the Medical Provider's location, phone number, and specialty. Furthermore, the user will be able to identify if the medical provider is designated for the patient's follow-up care. This information may be searched through the use of the Medical Provider Finder. This finder performs the same as the Patient Finder described above. The two finders are specific for either the patient or the medical provider.

The Patient Check List is a repository of significant dates which are related to the patient's medical information and treatment schedule. Dates regarding the first and last contact with the patient, when the out-of-town mailer was sent, consent forms signed, medical and lab records received, and dates of when medical, nutritional and educational instruction was presented to patients are maintained. The system will automatically generate and update several of these dates specifically in regards to treatment dates and dates of first and last contact. The users will enter in the other dates as applicable.

The information gathered regarding the patient's History and Physical is subdivided into six sections. The History & Physical General Information form includes data concerning the patient's eye color, overall physical condition, overall mental status, ethnicity or race, date since the onset of the disease and allergies that they might have. The History section contains information regarding the patients' drinking and smoking habits, social habits, and specific medical history. The Medical Provider uses the Physical portion of the History and Physical to place details about the patient's specific physical findings at the time of examination. The specific areas include the head, eye, ears, nose, throat, neck, and lungs. The Family History Medical record contains information of familial disorders and diseases. The form Family Genealogy is used to record if relatives are living or deceased and if deceased, the age of death. The last section, Home Medications, is where details are placed regarding the medications the patient takes at home as well as the dosage, frequency, and route of administration of these medications.

The Ocular Information is entered in three specific areas comprised of Prior History, Diagnostic Exams and Eye Exams. The Prior History form is subdivided into Physical Findings, Symptoms, and Diagnosis sections. All three sections provide for the user to select detailed entries from a list for a physical finding, symptoms or diagnosis. The Diagnosis may be entered by either ICD9 code or by selecting a description. Each section provides entry fields for which eye was examined and the date of examination. The Diagnostic Exams forms is used to input Prior Tests and Prior Treatment the patient may have received for ocular care. Data entries are again selected from a list and fields are provided to input which eye was examined and the date of examination. An Eye Exam List form is viewable to display a chronicle of previous eye exams the patient has had and then to quickly locate the associated record. The Eye Exam form itself allows for input of BSCVA, Visual Acuity, Subdivision, Contrast Sensitivity, IOP, Refraction Sphere, Refraction Cylinder, Refraction Axis, Pepper Test and the results of the Color Test. The form is partitioned into two panels. One panel is for right eye data (OD) and the other panel for left eye data (OS).

The Treatments section consists of several forms for user input concerning information relevant to medical orders, treatment details, patient questionnaire, and quality insurance. A Treatment List form is viewable to quickly display a chronicle of previous treatments the patient has had to date and then to quickly locate the associated records. Furthermore, a Medical Provider may initiate a treatment regime for a new patient or add a treatment for an existing patient from this form. A record for Standing Orders is placed at the top of the hierarchy beneath the Treatments category. The Standing Orders are typically default orders that the Medical Provider will supply should specific events or medical responses occur with regard to all of their patients' treatments. Displayed below the Standing Orders are icons to indicate the dates that treatments were initiated for a patient. If a treatment had to be canceled for medical reasons, this date will be designated with a distinct icon.

For each treatment date there is an associated form for RT Orders, Medication Orders, Discharge Instructions, Questionnaire, Flow Sheet 1, Flow Sheet 2, and Lot Tracking. The RT Orders record contains the Pretreatment Orders section for orders such as laboratory blood analysis and the Treatment Orders section for orders pertinent to fluid volume maintenance, anticoagulants and patient monitoring. The Medication Orders form records treatment data relevant to fluid replacement and anticoagulants. The Discharge Instructions provide patient information for post treatment home care. To document patient response and improvement as the RheoTherapy® treatment progresses, a Questionnaire form is provided. Here changes in the patient's mental and physical conditions are recorded. Flow Sheet 1 will retain specific patient information such as pre and post treatment vital signs and specific infusion machine data including machine serial numbers. Flow Sheet 2 will be for recording patient and machine conditions at timed intervals over the course of the treatment. Additionally, the total volume removed and the total volume replaced are reported on Flow Sheet 2. The Lot Tracking form is used to input applicable information for supply items regarding lot numbers, manufacturers and expiration dates of materials.

The Lab Results form is used to report the patient's blood laboratory analysis at different stages of treatment. A Lab Results List form is viewable to display a chronicle of previous lab results the patient has had and then to quickly locate the associate record. Specific laboratory tests may be grouped into a category referred to as Rheofactors. Rheofactors are laboratory tests that have been associated with specific patient responses as a result of RheoTherapy®. These tests include Total Cholesterol, Fibrinogen, HDL and IgA analysis.

Word processing documents that are associated with individual patients may be stored in the local database. These files are located under the Documents category. A Documents List form is viewable to display a chronicle of word processor files that have been retained for the patient and to quickly locate the associated record. Files may be added to or deleted from the patient's records from this form. Data gathered in the forms will be uploaded to a central repository periodically by the user. If after a given period the user has not uploaded the data, the system will prompt them to perform this simple procedure. with a single mouse click, the data is retrieved from the local Access database and passed through the Internet to the central repository where the Internet Information Server and Microsoft Transaction Server seamlessly coordinate to store the data on a SQL Server. After the data has been transferred to the central repository, the user may disconnect from the Internet. All of the data processing necessary takes place without user intervention or loss of valuable time. In a similar fashion, reports will be produced at the central repository and returned to the user.

Reports from the system database may be generated at either the local or the Internet level. The Patient Treatment Summary Report and the Patient Response Report will be local reports. The Patient Treatment Summary Report will present the Treatment Number, Date and Total Volume Removed for each treatment for a given patient. The Patient Response Report will display an analysis of how the patient's eyes have responded to RheoThera® treatment based upon a comparison of eye examinations and questionnaires from pre treatment and post treatment data.

Three reports may be generated at the local or Internet level and will consist of the Overall Improvement Report, Period Summary Report and the QI Report. The Overall Improvement Report will present the number of Eyes Treated and the Percent Improved for nine predetermined diseases. Again, a pre treatment and post treatment analysis of the data will be performed. The Period Summary Report will summarize in chart form the treatments administered with respect to the Total Number of Patients Treated and the Total Number of Treatments Provided for a set time Period. Furthermore, for this time period, the Total Number of Patients Treated for each of nine predetermined diseases will also be reported in a table. The QI Report will be used to summarize the number of adverse events that occurred during the treatment of a patient. The Patient Prognostication Report is only an Internet report. The local database does not contain sufficient information to produce a meaningful report. This report is utilized to provide the patient with information regarding how other patients with similar History, Diagnosis and Rheologic Factors have responded to RheoTherapy®. The Patient Prognostication Report is generated from data the system retrieves from the central database repository of all records for all patients. Other patients are matched to a potential patient's profile based upon specific criteria and data is then aggregated and analyzed to generate a possible treatment prognostication.

By providing both local and Internet database support, licensed users of the system will be able to maintain patient charts and records as well as contribute to and benefit from data aggregation that results in a compendium of information relating to the effects and benefits of RheoTherapy®.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Example of an Apheresis Session

During an apheresis session, a patient reclines in a comfortable blood donation chair and intravenous (IV) lines are introduced, one into the antecubital vein of each of his or her forearms. (Single arm access methods and central lines or PIC lines are also possible but are less desirable). The IV catheters are either 17 gauge steel needles or 14 gauge plastic IV catheters, depending upon the caliber and location of the blood vessels to be cannulated. Blood is optimally withdrawn and circulated from the patient at a rate in the range of 75 to 150 cc/min. The time to complete an apheresis procedure of this invention varies from patient to patient, and from day to day depending upon numerous variables. However, the average time required to process 80% to 120% of a typical patient's plasma volume, usually requires 1.5 to 2.5 hours for the average AMD patient, who serves as the prototypical example.

The blood is pumped out of the body via an extracorporeal circuit, through the apheresis pumping equipment, including any membrane differential filters, and then back into the body. Usually only about 250 cc of a patient's blood is located within the extracorporeal circuit tubing at any given time during the procedure. As will be known to persons skilled in the art, there are several types of apheresis procedures that can be used to alter the blood's rheology. Each type has its benefits and drawbacks.

Plasma exchange, as practiced in the context of the present invention, can be conducted using replacement solutions containing primarily 5% human albumin mixed with saline and Hespan®; selective adsorption is conducted using a tryptophan-polyvinyl alcohol adsorber (TR-350 from Asahi Medical), and membrane differential filtration is performed using the paired hollow fiber filters, e.g. the Rheo-Filter AR2000 and the OP-05 plasma separator. In each case, the plasma separation device operates to divide the whole blood's cellular fraction from the plasma fraction. In plasma exchange, the plasma is iteratively removed via sequential filtering steps with a centrifuge or hollow fiber filter device. The plasma portion is discarded and can be replaced with a solution of saline/HES and 5% human albumin. The targeted high molecular weight proteins are depleted but so are the other plasma components. Therefore, the efficiency of this system is comparatively less than that of the MDF system. In addition, the costs to perform plasma exchange are also significantly higher than MDF filtration.

Immune adsorption is also usable but sensitization to column components provides a significant patient safety risk compared to MDF systems. Therefore, it has been determined that the MDF system is both safer, easier, more efficient, faster and less expensive that any other available system in the market today, and is therefore the apheresis treatment system of choice for the performance of the present invention.

As described herein, the MDF system has been shown to significantly reduce plasma concentrations of numerous circulating macromolecules, including alpha-2 macroglobulin, triglycerides, the cholesterol superfamily of beta-lipoproteins, various immunoglobulins, fibrinogen, AGE-modified lipoproteins, and the like.

Persons skilled in the art will know to administer anticoagulants, such as heparin injected as a bolus prior to therapy, followed by a continuous infusion, and ACD-A (anticoagulant citrate diacetate) continuously infused at a ratio of 1:16 during the course of treatment. ACD-A is the generally preferred anticoagulant of choice in conventional apheresis for extracorporeal apheresis circuits, since it does not promote systemic anticoagulation effects in the patients being treated. When ACD-A is used, it is customarily accompanied by continuous infusion and/or ingestion of calcium to prevent systemic depletion of calcium ion, which can lead to numerous deleterious effects (myocardial excitability, muscular fasciculations and parasthesias).

Heparin Sodium (both low and high molecular weight versions) can be used in place of ACD-A, and is the non-obvious yet preferred anticoagulant of choice in the present invention because of heparin's actions within a patient's systemic circulation as well as throughout the extracorporeal circuit, and over-heparinization can lead to excessive bleeding in a patient. However, if over-heparinization does occur, such effects can be safely and quickly neutralized with the administration of medications such as Vitamin K infused intravenously.

In the preferred embodiment of the present invention, Heparin Sodium is provided as an initial bolus, then as a continuous infusion determined by the standardized formula involving the patient's weight. Generally less than a total of 15,000 IU (international units) of Heparin Sodium are necessary to maintain appropriate levels of anticoagulation throughout the apheresis procedure of the present invention. The anticoagulation status of the patient is monitored frequently (ACT test) throughout the procedure and afterwards in order to ensure appropriate anticoagulation within the established limits of safety for extracorporeal circuit therapies, e.g., cardiac bypass machine circuits, etc.

A preferred embodiment of the present invention provides for continuous measurement of pulse, blood pressure, and oxygen saturation, as well as intermittent measurement of temperature and respiration. In addition, it is preferred that the patient be continuously connected to an EKG monitor capable of automatically detecting and documenting anomalous cardiac rhythms for further evaluation. Apheresis in the present invention is complete when approximately 80% to 120% of a patient's plasma volume has been treated in a single session. However, any deterioration of the patient's clinical status in terms of pulse, blood pressure, oxygen saturation, temperature, respiration, or heart function, or the treatment nurse's ongoing clinical assessment, may result in premature termination of the procedure prior to reaching this target.

After treatment, the patient is monitored while resting for approximately an hour, consuming fluids and a snack. If uneventful, only then is the patient discharged. Patients are instructed not to drive for 24 hours.

As illustrated in FIG. 1, and as stated above, post-treatment evaluation is the foundation of continuous improvement in the integrated apheresis treatment process and business method and business method of delivery of this invention.

Rheopheresis® treatments preferably are administered in a period ranging from about one day to about ten days, such that at least about 200% of a patient's plasma is processed during about a one-week period of time. Persons skilled in the art will understand that treatment provided only once per month likely will be insufficient to improve clinical outcomes and that treatments provided on a daily basis or even up to about two times per week may be debilitating to a patient in the sense that they deplete excessive amounts of high molecular weight plasma components. However, relatively more frequent Rheopheresis® blood filtration treatments would be appropriate in acute situations, as discussed below.

TABLE 1 shows the "Mean Elimination Kinetics of the RheoFilter MDF System"
Mean Elimination Kinetics of the VasoFilter MDF System*

| Parameter | Membrane Filtration % | | | | | | |
|---|---|---|---|---|---|---|---|
| Proteins/Lipoproteins | Brunner[1] | JJA[2] | Utah[3] | Tauch[4] | SBP[5] | Gode[6] | Mass[7] |
| Total Protein | −19 | −13 | −27 | −15 | | −23 | −23 |
| Albumin | −4 | −2 | −28 | | | | |
| Total Cholesterol | −53 | −76 | −46 | | −44 | −53 | −54 |
| Triglycerides | +2 | −62 | −58 | | −34 | | |
| LDL-Cholesterol | −67 | −100 | −66 | | −49 | −57 | −60 |
| HDL-Cholesterol | −38 | −15 | −29 | | −31 | −42 | −43 |
| VLDL-Cholesterol | −6 | −95 | −55 | | | | |
| Lp(a) | | −87 | | | | | |
| Apolipoprotein $A_1$ | | −19 | | | | | |
| Apolipoprotein B-100 | | −100 | | | | | |
| Plasmin | | −20 | | | | | |
| Alpha-2 Macroglobulin | −70 | −80 | | | | | |
| IgG | −34 | −17 | −32 | | | | |
| IgA | −41 | −40 | −39 | | | | |
| IgM | −67 | −91 | −58 | −36 | | | |
| C3 | | −31 | | | | | |
| C4 | | −42 | | | | | |
| Hematological | | | | | | | |
| Erythrocytes | −4 | | +3 | | | | |
| Leukocytes | +2 | | +93 | | | | |
| Platelets | −6 | | −12 | +1 | | | |
| Hemoglobin | −6 | | +3 | | | | |
| Hematocrit | −3 | | +4 | +2 | | | |
| MCV | +1 | | 0 | | | | |
| Coagulation | | | | | | | |
| Fibrinogen | −47 | −57 | −60 | | −56 | −54 | −55 |
| Fibronectin | | −74 | | | | | |
| PT | −7 | | | | | | |
| PTT | 0 | | | | | | |

TABLE 1-continued shows the "Mean Elimination Kinetics of the RheoFilter MDF System"
Mean Elimination Kinetics of the VasoFilter MDF System*

| Parameter | Membrane Filtration % | | | | | | |
|---|---|---|---|---|---|---|---|
| Proteins/Lipoproteins | Brunner[1] | JJA[2] | Utah[3] | Tauch[4] | SBP[5] | Gode[6] | Mass[7] |
| TT | −7 | | | | | | |
| Antithrombin III | −13 | | | | | | |
| Rheology | | | | | | | |
| Plasma Viscosity | −15 | | | | | | |
| Whole Blood Viscosity | −16 | | | | | | |
| Erythrocyte Aggregation | −55 | | | | | | |

*Plasmaflo ® OP-05W, and RheoFilter ® AR 2000, post- & pre-treatment serum concentration.
[1]Brunner et al., J. Artif. Organs (1995) 18, 794–798.
[2]Sonntag et al., Jpn. J. Apheresis (1997) 16, 26–30.
[3]Unpublished data from the University of Utah study (1998).
[4]Tauchert et al., Jpn. J. Apheresis (1997) 16, 34–37.
[5]Saito, International Society of Blood Purification, Nagoya (1900) 81–82.
[6]Godehardt et al., Prevention of Coronary Heart Disease International Symposium, Munich (1992) 208–2127.
[7]Messner et al., Prevention of Coronary Heart Disease International Symposium, Munich (1992) 204–207.

Table 1 is a composite presentation of research in the field measuring the ability of the Rheopheresis® system to deplete certain RAMs. Blood samples were drawn at different post-treatment intervals and provide only a trend analysis as opposed to a specific statement concerning the precise depletion capability. Of note, it is important to understand that every patient has different distribution kinetics, and their re-equilibration times vary significantly. Therefore, it is critical to measure these profiles with each patient at the suggested intervals so that the Rheopheresis® practitioner can establish the optimal treatment processing volume and inter-treatment interval for each patient on an individualized basis. Appropriate treatment dosing and scheduling must be tailored to each patient and to each disease process and the general protocol developed. Otherwise excessive RAM depletion can occur, resulting in immunocompromised patients, over-anticoagulation or under-treatment, thus reducing safety and/or clinical effectiveness. Table 1 shows the differences in the averages that were observed in relatively large numbers of samples. Individual depletion ranges can vary significantly from the means analysis.

Example 2

Treatment of AMD

The skilled artisan will understand that AMD serves as the prototypical model for chronic, age-related, degenerative, atherogenic, thrombotic or inflammatory diseases, especially those manifesting disturbances of blood rheology, of which other examples are mentioned above. The body of work, discussed above, by Brunner, Berrouschot and others generally supports the basis of the present invention that the depletion and/or removal of these blood proteins leads to numerous interrelated alterations in blood rheology, along with their secondary and tertiary effects. While these effects may be more generally distributed, in AMD the changes appear to promote a return to function in ostensibly senescent but otherwise viable cells in the posterior retina.

Drs. Swartz and Rabetoy (publication pending) conducted research at the University of Utah that demonstrated that select patients with Dry AMD who demonstrated significant improvement in their visual function after Rheopheresis® blood filtration had elevated pre-treatment baseline serum concentrations of certain rheologic protein markers. Data from this study is discussed below. A significant distinction between the therapeutic protocols of the present invention and others, e.g., the Brunner and Berrouschot protocols, is the length of the interval between subsequent even-numbered treatments. In the Brunner study, a 30-day interval was selected. Berrouschot was excessively aggressive providing 12 to 24 hour intervals. Brunner's interval was selected based upon the reimbursement policies in place at the German hospital system where the research was conducted and was not based on any scientific correlation of or regard for the maximization of therapeutic effects or rheologic kinetics. Berrouschot's protocol was designed to reduce acute macrovessel occlusion. The present inventor has discovered, unexpectedly, that this protocol feature can be altered to achieve dramatically improved clinical outcomes in diseases of the type described above that primarily involve the microcirculation as the therapeutic target of action.

Drs. Swartz and Rabetoy evaluated 30 patients with non-exudative AMD characterized by numerous large soft drusen. The patients were randomized into three groups of ten patients each: (1) an active treatment group; (2) a circuit ("sham column") group; and (3) a no-treatment control group. MDF treatments were performed with the Asahi filter system as described above. Apheresis patients (MDF and circuit) were evaluated over approximately 18 to 20 weeks while receiving ten protocol apheresis treatments. All patients underwent a battery of laboratory and ophthalmologic tests. "Improved vision" was defined as consistent, significant, correlated improvement in at least three of the following four visual assessment parameters: (1) 2.5 lines of BSCVA (best spectacle-corrected visual acuity) improvement in the Study Eye; (2) 2.5 lines of BSCVA improvement in both eyes; (3)>20% increase in PVSRT (Pepper Visual Skills for Reading Test) scores in at least one eye; and (4)>20% improvement in the VF-14 Questionnaire© scores. By this strict definition, "improved vision" occurred in four of the 30 patients studied. All four of the patients who improved were in the MDF treatment group. This represents 40% of that group, to a statistical power of p=0.023.

Within the MDF Treatment Group, a positive correlation was independently demonstrated between post-treatment "improved vision" and baseline serum levels of four rheologic markers identified as: total cholesterol, IgA, fibrinogen, and HDL cholesterol, (the latter being recognized as a substance known to be a potent vaso-protective agent primarily involved in reverse cholesterol transport). Higher baseline levels of any one of these factors were positively correlated with both the likelihood of improvement as well as the degree of associated total, post-treatment BSCVA line change. Five patients in the MDF treatment group presented with elevated baseline values of at least three of these four rheologic markers. Four of these five patients (80%) demonstrated "improved vision" exhibiting total increases in ETDRS line change (Study Eye+Fellow Eye) of 5.5, 6.0, 8.0, and 8.5 respectively. All four of these patients with "improved vision" presented with elevated baseline concentrations in all four (100%) of the rheologic markers mentioned above. This was considered to be highly significant.

The following case studies demonstrate the results of Rheopheresis® treatments in seven different patients with different types of AMD. The patients in these case studies were treated under protocols consistent with the foregoing description of the invention.

Case Study #1 Patient #1 was a sixty-six (66) year old female referred by her retina specialist in for consideration of RheoTherapy® for her AMD. She was first seen by this retina specialist on Apr. 11, 1997. At that time she complained of decreased vision in the right eye with metamorphopsia. At that time her vision was 20/50 OD and 20/50 OS. She had cataracts in both eyes. The fundus exam revealed a pigment epithelial detachment OD and a possible net. A fluorescein angiogram showed a PED OD and dry AMD OS and indocyanine green angiogram showed a sub foveal plaque. When she returned Dec. 3, 1997, her vision had deteriorated; she was having difficulty ready newspapers. At that time visual acuity was 20/200 OD and 20/30 OS. Fluorescein angiogram revealed a PED with no definite focal net. Left eye appeared normal. The retina specialist referred her for RheoThera® at that time. She had treatments on Jan. 6, 1998, Jan. 8, 1998, Jan. 19, 1998, Jan. 21, 1998, Feb. 17, 1998 and Feb. 19, 1998. She tolerated all these treatments well. After her first treatment she had noted significant improvement. She was more comfortable driving and was able to sit farther away from the television. She also noted improvement in her amsler grid and could see tiny threads on her mattress. She was very pleased with her therapy. She continued to improve with subsequent treatments and after four treatments was able to read with her bedside lamp for three to four hours at a time. The grayness had resolved and the amsler grid was clear. She returned to see her retina specialist on Feb. 25, 1998. She told him that her vision had improved but that she was still having difficulty with reading and watching television. At that time her vision had improved to 20/50 OD and 20/30 OS. She still had some metamorphopsia OD. Her fundus exam showed a PED but it had decreased in size on exam and the fluorescein angiogram showed mottled leaking but no evidence of definite PED. She has subsequently had two more treatments and is awaiting a follow-up visit with her retina specialist who has referred more patients to us.

Case Study #2

Patient #2 was a fifty-five (55) year old male referred by his optometrist for treatment of AMD. He was amblyopic and is blinded in his left eye. He was found to have dry AMD involving his right eye several years ago. His vision had worsened from 20/15 to 20/40. Patient #2 began his treatments Jan. 5, 1998 and had a second treatment on Jan. 7, 1998. On Jan. 13, 1998 he reported that he had returned to his optometrist and his vision had improved from 20/40 to 20/25 after only two treatments. His cholesterol had also dropped from 250 to 191. By the time he arrived for his third treatment on Jan. 26, 1998, he said his vision had already improved to 20/20. He was ecstatic. His fourth treatment was given on Jan. 28, 1998. He was seen by his primary optometrist on Jan. 30, 1998. The optometrist was very pleased with the results of RheoTherapy® treatments. As a result of the six (6) RheoTherapy® treatments, his visual acuity in his right eye improved from 20/40–2 to 20/20–1. The optometrist also noticed that the area around his macula had a better color and the scattered black pigment was more defined. On Feb. 3, 1998, he returned to see a retina specialist who had previously given him no hope. The specialist reported that the vision in the OD was 20/20. What the retina specialist found most significant was that the low contrast testing done in October, 1997 was 20/100 in the right eye and it had improved to 20/50–1 by Feb. 3, 1998 after only four RheoThera® treatments. The retina specialist also reported that Patient #2 mentioned improved vision, brighter color sensation and improved contrast after the first treatment. He also had an increased energy sensation and improved contrast after the first treatment. He also had an increased energy level. He subsequently had treatments on Feb. 23, 1998 and Feb. 25, 1998.

Case Study #3

Patient #3 was a sixty-four (64) year old male with a long history of central serous retinopathy. He has been seen multiple times in the past by a world renowned expert on macular disease. He had multiple laser treatments by this expert. His vision continued to deteriorate to the point where he could no longer function in his employment as a professional engineer. Visual acuity on Apr. 12, 1996 was 20/200 OD and 6/200 OS. He had his first RheoThera® treatments on Mar. 14, 1997 and Mar. 17, 1997. Repeat exam by the local retina specialist showed visual acuity of 20/50 OD. He could count fingers at two feet OS. He has had another seven (7) treatments. On Sep. 11, 1997, after a total of eight (8) treatments, visual acuity fluctuated between 20/30 and 20/40 OD and was 20/200 OS. Patient #3 stated that since his last visit he has had another eye exam and visual acuity is now 20/20 near vision and 20/30 distant vision. He was extremely pleased with his improvement because he is again able to function as an engineer. He was also again able to produce and interpret engineering drawings and drive an automobile.

Case Study#4

Patient #4 was a sixty-three (63) year old male who was diagnosed as having AMD by exam on Oct. 2, 1997. At that time, visual acuity was 20/25 OD and 20/40 OS. He had neovascularization in his right eye and a macular detachment in the left. On the fluorescein angiogram the subretinal neovascularization OD leaked slowly. His ophthalmologist offered no treatment since the leakage was in the area of the fovea. A report examination by the same physician on Oct. 23, 1997 revealed visual acuity of 20/25 OD and 20/60 DOS. On Nov. 13, 1997 visual acuity was 20/20 OD and had deteriorated to 20/100 OS. His ophthalmologist suggested RheoTherapy® treatment. After two (2) treatments he noticed a significant improvement and was reading with no difficulty. After four (4) treatments, he reported further improvement. Prior to treatment, he was unable to distinguish his cattle from each other and could not distinguish their shapes in the pasture. After four (4) treatments he was again able to do so which is very significant because he is a cattle rancher. He was again able to grade the cattle morphology to determine nutritional status. He previously was unable to distinguish anything with his left eye, and after four (4) treatments he was able to read large print with his left eye. A fluorescein angiogram done by the referring physician after four (4) treatments was reported as showing significant improvement. Patient #4 received a total of eight (8) treatments and now reported his vision as being 20/15 OD and 20/40 OS following those treatments.

Case Study #5

Patient #5 was a fifty-two (52) year old male with a history of familial macular drusen OU. Visual acuity was 20/300 OD and 20/200 OS Sep. 13, 1994. Fluorescein angiogram showed no neovascularization. At that time his ophthalmologist gave him no options for treatment. Best visual acuity on Apr. 23, 1997 was 20/400 OD and 20/200 OS. After four (4) RheoThera® treatments, he still had distortion of his vision but his vision adjusted more quickly after exposure to bright light than it had previously. A repeat visual exam after two (2) treatments revealed a visual acuity of 20/70 OD and 20/60 OS.

Case Study #6

Patient #6 was a seventy-three (73) year old male with a long history of AMD. He is blind in his left eye due to wet AMD. He has dry AMD in his right eye. Visual acuity OD was 20/50. Fundus exam by his retina specialist prior to treatment revealed dry macular degeneration and a few areas of chorioretinal atrophy in the right eye. He has undergone six (6)RheoTherapy® treatments. Between his first and second treatments, he had transient improvement in his vision in that objects appeared brighter. He then noticed no improvement through his fourth treatment. After no improvement with four (4) treatments he considered discontinuing therapy but decided to continue therapy for two (2) more treatments because so many people that had treatments when he did had noticed improvement. After his fifth (5) treatment he stated that he thought he could see golf balls better. His wife reported that he is now able to read standard sized print without a magnifying glass. He previously needed a magnifying glass. He is also able to read letters on chart moving his eyes from left to right where previously he had to shift his eyes left to right to "catch" all of the letters. He also reports significantly increased intensity of red on the traffic light. He previously stated he had to be told by his wife that the light was red.

Case Study #7

Patient #7 was a seventy-four year old male with a long history of dry AMD OD and wet AMD OS. Visual acuity was 20/400 OD and 20/30 OS on Aug. 29, 1995. On Dec. 17, 1997 visual acuity was hand motion OD and 20/400 OS. Patient #7 stated that his doctors offered him essentially no treatment. He had tried multiple low vision aids without any significant success. Despite laser photocoagulation OS in 1995, he had regrowth of the abnormal blood vessels and could not undergo repeat laser coagulation without increasing the size of the central blind spot. After eight Rheo-Therapy® treatments, he reports that the amount of light he detects continues to increase. He is now able to recognize faces when looking straight at the person. He was not able to do that previously. He reported that the blind spot in his left eye had fragmented and diminished in size and the wavy lines have straightened.

The use and general benefits of Rheopheresis® blood filtration for the treatment of AMD also is described in Davis et al., in Optometry Today (October 1998).

Example 3

Treatment of Atherosclerotic Disease

Atheromatous diseases develop as a result of lipid-laden plaques that slowly form preferentially within the intimal walls of coronary, carotid, aortic, pelvic, femoral, popliteal and other arteries throughout the body, often in the presence of disturbed lipid metabolism. Three protocols for treating these diseases according to the methods of the present invention follow:

First, as providing secondary prevention for the precipitation of acute vascular or thrombotic events (as in procoagulant cardiac patients considered "at risk" and/or those patients receiving dialysis treatments that predispose them to increased risks of thrombotic events and accelerated atherogenesis), long-term weekly or bi-weekly treatments according to the present invention are contemplated, depending upon individual patient responsiveness to treatments. Measurement of specific RAMs and the kinetics associated with their depletion within these patients will afford tight control of the procoagulant state. The long-term depletion is to be correlated with clinical symptoms as well as disease specific testing (angiograms, stress testing, plethesmography, tissue oxygenation, PET scans, etc.). This is similar to the dose adjustments provided in the long-term management of diabetic patients using insulin, however, such means have never been applied as in the present invention to community dwelling patients in out-patient apheresis settings who are afflicted with chronic, age-related, degenerative, atherogenic, thrombotic and/or inflammatory diseases associated with the accumulation and/or deposition of biological substances that result in or are associated with disturbances of blood rheology and intrinsic endothelial cell function.

Second, in the setting of a planned vascular manipulation or intervention (bypass surgery, PTCA, etc.), reducing the incidence of an acute event or subsequent reperfusion injury can occur by a "blood prep" treatment 12 to 48 hours before the planed intervention, followed by one treatment 24 to 48 hours post intervention and another 2 to 7 days following that. This will provide the maximal intravascular depletion of procoagulant substrate macromolecules integral to the occurrence of post operative vascular complications (restenosis and thrombosis).

Third, in the setting of an acute vascular event (thrombosis), large vessel occlusion dynamics will be partially improved by the method of Berrouschot. However, the microcirculatory insult will need both sooner treatment as well as longer-term therapy. Therefore, in accordance with the present invention, MDF apheresis treatments should be performed immediately upon the establishment of a thrombotic vascular complication without delay, certainly less than six hours and more preferably less than one hour post event. Also, in addition to the method of Berrouschot, the addition of at least 1 to 3 more treatments as described herein over the next 10 days must be implemented for the slow-phase recovery of vascular and other injured tissues. Preferably, the time interval between successive Rheopheresis® blood filtration treatments ranges from about one day to about ten days and the total plasma volume processed in any one week period is at least about 200% of a patient's total plasma volume.

Example 4

Treatment of Rheumatoid Arthritis

Rheumatoid arthritis results from the destructive inflammatory reactions occurring in a synovial pannus associated with elevated serum levels of Rheumatoid Factor, various inflammatory proteins, immunologic globulins, integrins, and other compounds that are also found to invade the synovial lining of the various joints involved. Elevations of these substances are concomitantly found in the blood of patients with the disease and are putatively causative. The protocol for treating this disease according to the methods of the present invention would be similar, if not substantially identical to that of AMD with acute exacerbations managed with an accelerated protocol of the type used in acute ischemic events described above.

Example 5

Treatment of Diabetes Mellitus

Diabetes mellitus is classically described as an autoimmune disease demonstrating profound pathological effects on the microcirculation and peripheral nervous system, with classically observed disruptions of blood rheology associated with aldose deposition, and other disruptions of carbohydrate metabolism measured in both the serum and tissues. While the present invention may be used chronically (weekly or biweekly) to minimize the progressive damage induced by diabetes, the most likely application will be in the use of the present invention as a treatment of acute complications of the disease. According to the methods of the present invention described above this would involve the use of protocols similar, if not substantially identical, to acute vascular ischemic events.

Example 6

Treatment of Alzheimer's Disease

Alzheimer's disease is associated with the formation of "neurofibrilary tangles" or accumulations of complex deposits comprised primarily of Tau proteins and beta-amyloid proteins in specific brain tissues, and may also be associated with decreased local blood flow to those same brain tissues. A protocol for treating this disease according to the methods of the present invention would be substantially similar to one or more of the protocols described above.

Example 7

Treatment of Shunt—Fistula Occlusions

Renal dialysis patients and other utilize vascular indwelling intravascular catheters, shunts and fistulas to provide vascular access for numerous serial extracorporeal procedures. Almost universally, these patients experience life-threatening clotting and occlusions of these access modalities. A protocol for treating this type of adverse thrombogenic event according to the methods of the present invention would be substantially similar to one or more of the protocols described above.

Although the present invention has been described in detail with reference to examples above, it is understood that various modifications can be made without departing from the spirit of the invention. Accordingly, the invention is limited only by the claims. All cited patents and publications referred to in this application are herein incorporated by reference in their entirety.

What is claimed is:

1. A method of providing membrane differential blood filtration treatment comprising:
   (a) evaluating a candidate patient to identify whether the patient has a RAM associated disease and to determine that state and extent of that disease;
   (b) determining whether the patient exhibits elevated plasma levels of at least two RAMs;
   (c) declining to treat patients with membrane differential blood filtration who are not likely to respond to treatment or who might be harmed by the treatment;
   (d) selecting a particular membrane differential blood filtration treatment protocol appropriate for chronic versus acute medical situations; and
   (e) providing membrane differential blood filtration treatment.

2. The method of claim 1 wherein the step of selecting a particular membrane differential blood filtration treatment protocol includes an evaluation of a database containing data on other patients treated by membrane differential blood filtration.

3. The method of claim 1, further comprising the step of providing disease-specific medical follow-up evaluations.

4. The method of claim 3, further comprising the step of submitting data on the patient to a database containing data on other patients treated by membrane differential blood filtration.

5. An integrated apheresis treatment process comprising the steps of:
   (a) providing at least one dedicated out-patient, non-hospital, apheresis treatment facility;
   (b) locating and selecting ambulatory, community-dwelling patients potentially capable of benefiting from apheresis treatments within a community that can be served by said apheresis facility;
   (c) identifying and selecting from among said patients, by means which include measurement of serum levels of circulating rheologically active macromolecules in said patients, a subset of patients capable of benefiting from apheresis treatments;
   (d) performing apheresis treatments in sessions on the selected patients in said dedicated out-patient apheresis treatment facility; and
   (e) determining clinical endpoints to said apheresis treatments based upon reductions in serum levels of said rheologically active macromolecules and correlations of clinical symptomatology through disease-specific testing and serial endpoint and clinical assessments.

6. An apheresis treatment method, comprising the steps of:
   (a) identifying chronically ill patients having age-related, degenerative, atherogenic, thrombotic or inflammatory diseases, said chronically ill patients being considered candidates for an apheresis procedure;
   (b) storing patient profile data for an identified chronically ill patient;
   (c) analyzing qualifying data for said identified chronically ill patient to determine applicability of an apheresis treatment; and
   (d) performing apheresis treatments in sessions on said identified chronically ill patient.

7. The method of claim 6, wherein step (b) further comprises the step of storing at least one of medical history data, physical characteristic data, medical condition data, diagnosis data, historical procedure data, and clinical effect data.

8. The method of claim 6, wherein step (c) further comprises the step of analyzing at least one of medical history data, disease specific history data, physical examination data, and interview data.

9. The method of claim 6, wherein step (c) further comprises the step of comparing patient profile data with a composite patient profile that is generated using data from similar patients who have completed an apheresis treatment process.

10. The method of claim 9, wherein step (c) further comprises the step of determining at least one of a probability of apheresis treatment success, a potential degree of anticipated clinical outcomes based upon statistical normograms from an analysis of historical composite patient profiles, and a most appropriate initial apheresis treatment protocol.

11. An apheresis treatment qualification method, comprising the steps of:

(a) identifying a chronically ill patient having an age-related, degenerative, atherogenic, thrombotic or inflammatory disease, said chronically ill patient being considered a candidate for an apheresis procedure;

(b) storing patient profile data for said identified chronically ill patient;

(c) receiving, from a centralized database system, a composite patient profile derived from other patients similarly situated to said identified chronically ill patient;

(d) comparing said patient profile data with said received composite patient profile; and (e) determining based upon the comparison in step (d), whether said identified chronically ill patient would likely benefit from apheresis treatments.

12. The method of claim 11, wherein step (b) comprises the step of storing at least one of medical history data, physical characteristic data, medical condition data, diagnosis data, historical procedure data, and clinical effect data.

13. A method of screening patients for a membrane differential blood filtration treatment comprising the steps of:

(a) identifying whether the patient has a RAM associated disease and determining that state and extent of that disease;

(b) determining whether the patient exhibits elevated plasma levels of at least two RAMs;

(c) selecting patients who are likely to respond to membrane differential blood filtration treatment or who will not be harmed by the treatment; and, optionally, (d) selecting a particular membrane differential blood filtration treatment appropriate for treating a specific RAM associated disease.

14. The method of claim 13, wherein the step of selecting a particular membrane differential blood filtration treatment further includes screening a database containing patient data from individuals treated by membrane differential blood filtration to determine the most appropriate treatment protocol.

15. The method of claim 13, further comprising the step of submitting data in a patient profile to a database containing patient data from other membrane differential blood filtration treatment patients.

* * * * *